(12) United States Patent
Lechleiter

(10) Patent No.: US 8,618,074 B2
(45) Date of Patent: Dec. 31, 2013

(54) GPCR ENHANCED NEUROPROTECTION TO TREAT BRAIN INJURY

(75) Inventor: James D. Lechleiter, San Antonio, TX (US)

(73) Assignee: Board of Regents of the University of Texas System, Austin, TX (US)

(*) Notice: Subject to any disclaimer, the term of this patent is extended or adjusted under 35 U.S.C. 154(b) by 282 days.

(21) Appl. No.: 12/531,410

(22) PCT Filed: Mar. 17, 2008

(86) PCT No.: PCT/US2008/057234
§ 371 (c)(1),
(2), (4) Date: Mar. 22, 2010

(87) PCT Pub. No.: WO2008/113072
PCT Pub. Date: Sep. 18, 2008

(65) Prior Publication Data
US 2010/0216735 A1      Aug. 26, 2010

Related U.S. Application Data

(60) Provisional application No. 60/918,535, filed on Mar. 15, 2007.

(51) Int. Cl.
*A61K 31/70* (2006.01)

(52) U.S. Cl.
USPC .................................. 514/49; 514/48; 514/51

(58) Field of Classification Search
USPC .................................................. 514/48, 49, 51
See application file for complete search history.

(56) References Cited

U.S. PATENT DOCUMENTS

| | | | |
|---|---|---|---|
| 3,846,402 A | 11/1974 | Eckstein et al. | |
| 5,236,908 A | 8/1993 | Gruber et al. | |
| 5,763,447 A | 6/1998 | Jacobus et al. | |
| 5,837,861 A | 11/1998 | Pendergast et al. | |
| 6,864,243 B1 | 3/2005 | Peterson | |
| 7,256,183 B2 | 8/2007 | Peterson et al. | |
| 7,285,658 B2 * | 10/2007 | Cook et al. | 536/26.2 |
| 2004/0059104 A1 | 3/2004 | Cook et al. | |
| 2004/0243101 A1 | 12/2004 | Gillis | |
| 2005/0009778 A1 | 1/2005 | Peterson | |
| 2005/0053612 A1 * | 3/2005 | Granstein et al. | 424/184.1 |

FOREIGN PATENT DOCUMENTS

| | | | |
|---|---|---|---|
| WO | 99/09998 | 3/1999 | |
| WO | WO 2006038865 A1 * | 4/2006 | C07H 19/04 |

OTHER PUBLICATIONS

"Definition of derivertive", retrieved from Merriam-Webster online dictionary <<http://www.merriamwebster.com/dictionary/derivative>> on Apr. 6, 2011, 2 pages.*

Brain Basics—Know your brain, Apr. 2001, pp. 1-10, National Institute of Neurological Disorders and Stroke, National Institutes of Health, U.S. Department of Health and Human Services.*
"Corticobasal Degeneration" from online publication by National Institute of Neurological Disorders and Stroke, National Institutes of Health, [retrieved on Oct. 4, 2011]. Retrieved from the internet <http://www.ninds.nih.gov/disorders/corticobasal_degeneration/corticobasal_degeneration.htm>, Published on Apr. 25, 2008.*
Transmissible Spongiform Encephalopathies from online publication by National Institute of Neurological Disorders and Stroke, National Institutes of Health, [retrieved on Oct. 4, 2011]. Retrieved from the internet <http://www.ninds.nih.gov/disorders/tse/tse.htm>. Published on Feb. 2, 2011.*
"Definition of analog", retrieved from Merriam-Webster online dictionary <<http://www.merriamwebster.com/dictionary/derivative>> on Oct. 5, 2011, 2 pages.*
Almdal et al., Arch Intern Med. 2004, 164, 1422-1426.*
Hindley et al., Journal of Neuroscience Research, 1994, 38, 399-406.*
Stella, ACS Symposium Series, 1975.*
Thornber, C. W., Chem. Soc. Rev., 1979, 8, 563-580.*
Harukuni et al., Neurol. Clin, 2006, 24, 1-21.*
Chorna et al "P2Y2 receptors activate neuroprotective mechanisms in astrocytic cells" Journal of Neurochemistry, 2004, vol. 91, pp. 119-132.
Lechleiter http://www.uthscsa.edu/csb/faculty/lechleiter.asp, Jul. 11, 2006.
Wu et al., "Inositol 1,4,5-triphosphate (IP3)-mediated Ca2+ release protects astrocytes from oxidative stress" Program No. 405.20, Abstract Planner of the 2004 Society for Neuroscience Conference in Washington, D.C.
Search Report for PCT/US2008/057234 Issued Sep. 23, 2008.
Written Opinion for PCT/US2008/057234 Issued Sep. 23, 2008.
International Preliminary Search on Patentability for PCT/US2008/057234 Issued Sep. 15, 2009.

* cited by examiner

*Primary Examiner* — Elli Peselev
(74) *Attorney, Agent, or Firm* — Meyertons, Hood, Kivlin, Kowert & Goetzel, P.C.; Eric B. Meyertons

(57) ABSTRACT

Disclosed are methods of preventing or treating neuronal damage associated with oxidative stress and/or neuronal injury. The method comprises administering to a patient a pharmaceutical composition comprising a purinergic P2Y receptor ligand, in an amount effective to increase the extracellular concentration of said agonist in the brain of the subject such that at least a portion of cell surface P2Y receptors expressed by astrocytes are activated to mount a neuroprotective response. The pharmaceutical composition may be administered orally or parenterally. The pharmaceutical composition with typically be administered to an individual within at least one hour of the event that caused oxidative stress in the subject. The pharmaceutical composition includes a P2Y purinergic receptor agonist, which can include uridine 5'-di- and triphosphate (UDP, UTP) and their analogs, adenosine 5'-diphosphate (ADP) and its analogs, cytidine 5'-di- and triphosphate (CDP, CTP) and their analogs, and dinucleoside polyphosphate compounds.

21 Claims, 15 Drawing Sheets

GPCR ENHANCED NEUROPROTECTION TO TREAT BRAIN INJURY

This application is a 371 of PCT Application PCT/US2008/57234, filed Mar. 17, 2008, which claims priority to U.S. Provisional Application Ser. No. 60/918,535, filed Mar. 15, 2007.

BACKGROUND OF THE INVENTION

1. Field of the Invention

The present invention generally relates to the field of therapeutics. More specifically, the invention relates to methods for neuroprotection in the brain.

2. Description of the Related Art

The central nervous system (CNS) is particularly vulnerable to insults that result in cell death or damage in part because cells of the CNS have a limited capacity for repair. As a result, disorders of the CNS often result in debilitating and largely irreversible degradation of a patient's cognitive and sensorimotor functions. Conditions that result in nerve cell death and damage range from degenerative disorders (e.g., Alzheimer's disease), ischemic episodes (e.g., stroke), or trauma.

Injury to the central nervous system (CNS) is an important cause of death and disability worldwide. For example, stroke is the third leading cause of death and disability in the U.S., with an estimated incidence of 700,000 cases annually. Two-thirds of stroke patients survive the first year following stroke, for an average of seven years, leading to more than 4.8 million stroke survivors currently in the U.S. Stroke costs the U.S. economy in excess of $30 billion per year in terms of medical costs and lost wages.

After several hours, little can be done to prevent the direct damage to the CNS caused by CNS disorders. For example, stroke treatments must typically be administered within six hours of onset. Depending on where the injury occurs in the brain, patients may be paralyzed on one side, may lose the ability to speak or see, and may have difficulty walking, among other symptoms. Gradual recovery of these functions is common, although recovery may be incomplete, and depends on the size and location of injury, among other factors.

Since damaged brain tissue does not regenerate, recovery must come from the remaining intact brain, which reorganizes itself, or rewires, in order to compensate for some of the function lost by the damage. Indeed, studies in animals and humans provide ample evidence of such reorganization of brain function following stroke. In particular, remaining neurons in both the damaged hemisphere and in the opposite intact hemisphere grow new processes (both axons and dendrites) and form new connections (synapses), which most likely contribute to recovery.

Stroke treatment has focused on limiting the extent of damage within the first few hours. Stroke is generally caused by a blockage of an artery leading to the brain, resulting in the death of brain cells supplied blood by that blocked artery. Current treatments for stroke have centered on treatments to prevent arterial blockages (control of blood pressure, lipids, heart disease, etc.), and treatments to prevent brain damage once the blockage has occurred. These latter treatments include "thrombolytic agents" ("clot busters" such as tPA) to break up arterial clots, and "neuroprotective agents," designed to protect brain tissue at risk for stroke. Such thrombolytic and neuroprotective agents must be administered within hours after the onset of stroke in order to be effective. Methods currently available for promoting recovery from CNS damage allow only partial recovery of neurological functions. In patients suffering from debilitating neurological deficits, incremental improvements in function may have a significant effect on quality of life. Given the large number of affected patients and the limitations of current methods, there is an urgent need for additional and improved methods to promote recovery from damage to the nervous system.

The classical role of astrocytes is to protect and support neurons. Astrocytes are present in significantly higher numbers than neurons in the adult brain and play an important role in brain homeostasis. Additionally, astrocytes are likely participants in information processing. Following synaptic activity, astrocytes buffer perisynaptic $K^+$ and remove extracellular glutamate by means of ATP-dependent membrane transporters. During oxidative stress, neuronal glutathione levels (GSH) are rapidly depleted and its re-synthesis is dependent on GSH production in and efflux from astrocytes. These physiological functions require that astrocytes be capable of rapidly responding to changes in neuronal activity and requirements with increased metabolic activity.

Astrocytes express receptors for a variety of neurotransmitters that are released from either neurons or glial cells. ATP/ADP appears to be the predominant extracellular signaling molecule in astrocytes. Both metabotropic (P2Y) and ionotropic purinoreceptors (P2X) are expressed in astrocytes and activation of either receptor subfamily results in increased intracellular $Ca^{2+}$. The metabotropic inositol triphosphate ($IP_3$) signaling pathway provides a mechanism whereby local extracellular signals can be rapidly transduced into increased intracellular ATP. G-protein linked receptors increase the production of $IP_3$, triggering release of $Ca^{2+}$ from thapsigargin sensitive stores in the endoplasmic reticulum (ER). $IP_3$-mediated $Ca^{2+}$ release can, in turn, increase mitochondrial $Ca^{2+}$ and consequently, increase respiration and ATP production. The production of intracellular ATP via $Ca^{2+}$-induced activation of matrix dehydrogenases is very rapid, occurring at levels ten-fold faster than stimulation by feedback from ATP/ADP pools. Although mitochondrial $Ca^{2+}$ uptake can increase ATP production, $IP_3$-mediated $Ca^{2+}$ release has also been shown to sensitize cells to apoptotic stimuli. Reports by Bernadi and co-workers suggest that this increased sensitivity, in part, can be attributed to $Ca^{2+}$ sensitive sites on the adenine nucleotide translocator, which under some circumstances plays a role in the mitochondrial permeability transition. Thus, an ATP-mediated increase in intracellular $Ca^{2+}$ release can signal either cell survival or cell death for an astrocyte.

SUMMARY OF THE INVENTION

The present invention provides a method of preventing or treating brain damage associated acute injury, e.g. stroke, as well as longer term diseases of the CNS. The treatment method includes promoting the neuroprotective function of astrocytes and enhancing the resistance thereof to both acute injury and longterm stress.

In a first set of non-limiting embodiments, a method for treating oxidative associated diseases of the CNS in a subject may include administering to the subject requiring treatment for such a disease a pharmaceutical composition comprising at least one P2Y receptor ligand, in a therapeutically effective amount to activate P2Y receptors on the surface of at least a portion of astrocytes in the affected area of the brain to mount a neuroprotective response. In an embodiment, the amount of P2Y receptor ligand administered to the patient will be sufficient to initiate $IP_3$-mediated $Ca^{2+}$ release in at least a portion of astrocytes affected by the brain injury. In an embodiment, administration of a P2Y-R agonist to a subject in accordance with the treatment methods described herein rapidly and transiently increase oxidative metabolism in affected astrocytes. In some embodiments, a P2Y-R agonist may be administered to a patient up to 24 hours following an injurious event. More typically, a P2Y-R agonist may be administered to a patient within 2 hours of brain injury. In other embodiments, a P2Y-R agonist may be administered to a subject prophylactically, or as part of an ongoing therapeutic regimen.

In a second set of non-limiting embodiments, a method for treating oxidative associated diseases of the CNS in a subject may include administering to the subject requiring treatment for such a disease a pharmaceutical composition comprising an agent capable of evoking $IP_3$-mediated $Ca^{2+}$ release in astrocytes, wherein said agent is provided in a therapeutically effective amount to initiate $IP_3$-mediated $Ca^{2+}$ release in at least a portion of astrocytes in the affected area of the brain, and thereby to mount a neuroprotective response. In an embodiment, an agent capable of initiating $IP_3$-mediated $Ca^{2+}$ release in astrocytes may include an agonist to one or more G-protein coupled receptors (GPCR). Such agents may include, without limitation, agonists to the following G-protein coupled receptors, all of which have been shown to stimulate $IP_3$-mediated $Ca^{2+}$ release in astrocytes: metabotropic glutamate receptors (mGluRs), epinephrine receptors $\alpha_1$-AR and $\alpha_2$-AR, GABA receptors $GABA_A$ and $GABA_B$, acetylcholine receptors $M_1$ and $M_3$, histamine receptor $H_1$, substance-P receptor $NK_1$, bradykinin receptor $B_2$, endothelin receptors $ET_A$ and $ET_B$, serotonin receptor $5-HY_{2C}$, oxytocin receptor, vasopressin receptor $V_1$, prostanoid receptor FP-R, vasoactive intestinal peptide receptor, angiotensin II receptor $AT_1$, µ- and κ-type opioid receptors, and benzodiazepine receptors. The therapeutically effective amount of such an agent will generally be sufficient to evoke IP3-mediated $Ca^{2+}$ signaling in at least a portion of astrocytes in the affected area of the brain.

Optionally, an agent capable of initiating $IP_3$-mediated $Ca^{2+}$ release in astrocytes may be administered concurrently with a P2Y-R agonist.

Non-limiting examples of oxidative associated diseases of the CNS that are amenable to treatment in accordance with the presently described methods include stroke, focal cerebral ischemia, global cerebral ischemia, cerebral ischemic episodes, micro/mini strokes that are undetected by Magnetic Resonance Imaging (MRI), ischemic reperfusion injury, operative ischemia, traumatic hemorrhage (for example a hypovolemic stroke that can lead to CNS hypoxia or anoxia), oxygen toxicity, neurodegenerative damage associated with Parkinson's disease, ageing, Alzheimer's disease and HIV dementia; autoimmune neurodegeneration of the type that can occur in encephalitis, and hypoxic or anoxic neuronal damage that can result from apnea, ageing, respiratory arrest or cardiac arrest, and anoxia caused by drowning, brain surgery or trauma (such as concussion or spinal cord shock).

The pharmaceutical compositions useful in this invention comprise P2Y receptor agonists. Exemplary though non-limiting P2Y agonists suitable for use in preparing pharmaceutical preparations may include uridine 5'-di'- and triphosphate (UDP, UTP) and their analogs (Formulae Ia and Ib), 5'-adenosine monophosphate (AMP) and its analogs, adenosine 5'-di- and triphosphate (ADP, ATP) and their analogs (Formulae IIa and IIIb), and cytidine 5'-di- and triphosphate (CDP, CTP) and their analogs (Formulae IIIa and IIIb). P2Y agonists also include dinucleotide polyphosphate compounds of general Formula (IV). Examples of P2Y agonists that may be useful for treatment and/or protection of brain injury include 2-MeSADP and N-methanocarba-2MeSADP ("MRS2365").

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which.

Figure 1A:
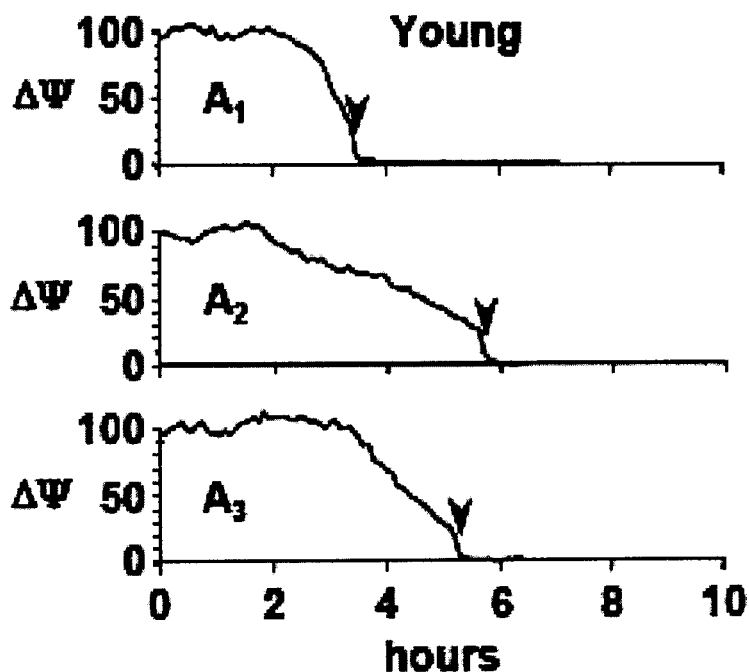
FIG. 1A depicts line plots of the mean TMRE fluorescence (ΔΨ) for the young astrocytes.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Definitions

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a linker" includes one or more linkers. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below, or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "organ", when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

The "central nervous system" (CNS) as used herein, refers to any component of the central nervous system including the brain and spinal cord, the cells and extracellular materials and fluids.

As used herein the terms "reducing," "inhibiting" and "ameliorating," when used in the context of modulating a pathological or disease state, generally refers to the prevention and/or reduction of at least a portion of the negative consequences of the disease state.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Pharmaceutically acceptable acid addition salts of the compounds of the invention include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," J. of Pharmaceutical Science, 1977; 66:1 19. The acid addition salts of the basic compounds are prepared by contacting the free base form with a sufficient amount of the desired acid to produce the salt in the conventional manner. The free base form may be regenerated by contacting the salt form with a base, and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention. Lists of suitable salts are found in Remington's Pharmaceutical Sciences, 17th ed., Mack Publishing Company, Easton, Pa., 1985, p. 1418, the disclosure of which is hereby incorporated by reference.

The phrase "combination therapy" (or "co-therapy"), as used herein embraces the administration of two or more therapeutic agents as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). The term is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a pharmaceutical preparation having a fixed ratio of each therapeutic agent or in multiple preparations for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues, e.g. intranasal routes, or eye drops. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, additional pharmacologic agents) and non-drug therapies (such as, but not limited to, surgery or radiation treatment).

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intraperitoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the terms "subject" generally refers to a mammal, and in particular to a human.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

By "prophylactically effective amount" is meant an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

The term "pharmacologically inert," as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

As used herein, the term "reperfusion injury" generally refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function. The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia. Reperfusion injury plays a part in the ischemic damage caused to neuronal tissue stroke and brain trauma. In prolonged ischemia (60 minutes or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Excessive nitric oxide produced during reperfusion reacts with superoxide to produce the potent free radical peroxynitrite. These radicals attack cell membrane lipids, proteins, and glycosaminoglycans, causing further damage.

As used herein, the term "oxidative stress" generally refers to an imbalance between the production of reactive oxygen and a biological system's ability to readily detoxify the reactive intermediates or easily repair the resulting damage. All forms of life maintain a reducing environment within their cells. The cellular redox environment is preserved by enzymes that maintain the reduced state through a constant input of metabolic energy. Disturbances in this normal redox state can cause toxic effects through the production of peroxides and free radicals that damage all components of the cell, including proteins, lipids, and DNA.

In humans, oxidative stress is involved in many diseases, such as atherosclerosis and Alzheimer's disease and it may also be important in ageing. However, reactive oxygen species can be beneficial, as they are used by the immune system as a way to attack and kill pathogens and as a form of cell signaling. In chemical terms, oxidative stress is a large increase (becoming less negative) in the cellular reduction potential, or a large decrease in the reducing capacity of the cellular redox couples, such as glutathione. The effects of oxidative stress depend upon the size of these changes, with a cell being able to overcome small perturbations and regain its original state. However, more severe oxidative stress can cause cell death and even moderate oxidation can trigger apoptosis, while more intense stresses may cause necrosis. A particularly destructive aspect of oxidative stress is the production of reactive oxygen species (ROS), which include free radicals and peroxides. Examples of ROS include .$O_2$—, superoxide anion; $H_2O_2$, hydrogen peroxide; .OH, hydroxyl radical; ROOH, organic hydroperoxide; RO., alkoxy and ROO., peroxy radicals; HOCl, hypochlorous acid; and OONO—, peroxynitrite. Some of the less reactive of these species (such as superoxide) can be converted by oxidoreduction reactions with transition metals or other redox cycling compounds including quinones into more aggressive radical species that can cause extensive cellular damage. Most of these oxygen-derived species are produced at a low level by normal aerobic metabolism and the damage they cause to cells is constantly repaired. However, under the severe levels of oxidative stress that cause necrosis, the damage may lead to ATP depletion.

The term "astrocyte" generally refers to a sub-type of GFAP-expressing glial cells in the brain. Astrocytes have a number of functions important for proper regulation and function of the CNS. Some of the functions for astrocytes include: Structural—astrocytes are involved in the physical structuring of the brain; Metabolic support—astrocytes provide neurons with nutrients; Blood-brain barrier—astrocyte perivascular foot processes encircling endothelial cells of the cerebral vasculature form part of the blood-brain barrier; Transmitter reuptake and release—astrocytes express plasma membrane transporters such as glutamate transporters for several neurotransmitters, including glutamate, ATP and GABA (More recently, astrocytes were shown to release glutamate or ATP in a vesicular, $Ca^{2+}$-dependent manner); Regulation of ion concentration in the extracellular space— astrocytes express potassium channels at a high density; when neurons are active, they release potassium, increasing its extracellular concentration. Because astrocytes are so permeable to potassium, they rapidly clear its excess accumulation in the extracellular space; Modulation of synaptic transmission—in the supraoptic nucleus of the hypothalamus, rapid changes in astrocyte morphology have been shown to affect heterosynaptic transmission between neurons; Vasomodulation—astrocytes may serve as intermediaries in neuronal regulation of blood flow; Promotion of the myelinating activity of oligodendrocytes—electrical activity in neurons causes them to release ATP, which serves as an important stimulus for myelin to form. In response to injury, astrocytes may also play critical roles in water movement and can both alleviate and/or exacerbate edema formation and consequent brain swelling subsequent to trauma and injury.

As used herein, the term "purinergic receptor" generally refers to a family of cell surface receptors which are activated by purine-containing compounds such as adenosine and the nucleotides ATP and UTP. The members of the family are broadly classified as follows: P2X receptors are ligand-gated ion channels; P1 receptors are adenosine-activated G protein-coupled receptors; and P2Y receptors, which form the basis of this application, are nucleotide-activated G protein-coupled receptors.

The term "P2Y receptor" or "P2Y-R" generally refers to a class of G protein-coupled purinergic receptors that are stimulated by nucleotides such as ATP (P2Y2, P2Y11), ADP, UTP (P2Y2, P2Y4), UDP (P2Y6) and UDP-glucose. To date, 8 P2Y receptors have been cloned in humans: P2Y1, P2Y2, P2Y4, P2Y6, P2Y11, P2Y12, P2Y13 and P2Y14. P2Y receptors are present in almost all human tissues where they exert various biological functions based on their G-protein coupling. The biological effects of P2Y receptor activation depends on how they couple to downstream signalling pathways, either via Gi, Gq or Gs G proteins. Human P2Y receptors have the following G protein coupling: Gq/11 coupled: P2Y1, P2Y2, P2Y6, P2Y14; Gi and Gq/11 coupled: P2Y4 Gs and Gq/11 coupled: P2Y11; Gi coupled: P2Y12, P2Y13.

As used herein, the term "receptor agonist" is generally used to refer to a synthetic or naturally occurring molecule that mimics the action of an endogenous biochemical molecule (such as hormone or neurotransmitter) when bound to the cognate receptor of that hormone or neurotransmitter. An agonist is the opposite of an antagonist in the sense that while an antagonist also binds to the receptor, the antagonist does not activate the receptor and actually blocks it from activation by agonists. A partial agonist activates a receptor, but only produces a partial physiological response compared to a full agonist. A co-agonist works with other co-agonists to produce the desired effect together. Receptors can be activated or inactivated by endogenous (such as hormones and neurotransmitters) or exogenous (such as drugs) agonists and antagonists, resulting in stimulating or inhibiting the cell. Thus, in the context of the present application, the term "P2Y receptor agonist" generally refers to any molecule that binds to P2Y receptors and elicits at least a portion of the cellular responses typically associated with P2Y receptor activation in that cell type. Non-limiting examples of purinergic agonists suitable for use in the presently described embodiemnts are set forth in detail below.

As used herein, the term "agent capable of evoking $IP_3$-mediated $Ca^{2+}$ release in astrocytes" generally refers to any agent that, when administered to astrocytes, stimulates IP3 signal transduction and mobilizes $Ca^{2+}$ from storage organelles. Therefore, an agent capable of evoking $IP_3$-mediated $Ca^{2+}$ release in astrocytes encompasses not only P2Y-R agonists, but also any agonist capable of stimulating G-protein coupled receptors in astrocytes as well as any agonists capable of stimulating non-G-protein couple receptors (e.g. tyrosine kinase receptors) or any agonists capable of stimulating phospholipase C enzymes which could directly increase $IP_3$. Such agents may include, without limitation, agonists to the following G-protein coupled receptors, all of which have been shown to stimulate $IP_3$-mediated $Ca^{2+}$ release in astrocytes: metabotropic glutamate receptors (mGluRs), epinephrine receptors $\alpha_1$-AR and $\alpha_2$-AR, GABA receptors $GABA_A$ and $GABA_B$, acetylcholine receptors $M_1$ and $M_3$, histamine receptor $H_1$, substance-P receptor $NK_1$, bradykinin receptor $B_2$, endothelin receptors $ET_A$ and $ET_B$, serotonin receptor $5\text{-}HY_{2C}$, oxytocin receptor, vasopressin receptor $V_1$, prostanoid receptor FP-R, vasoactive intestinal peptide receptor, angiotensin II receptor $AT_1$, µ- and κ-type opioid receptors, and benzodiazepine receptors.

A "stroke" as used herein generally refers to a serious medical condition characterized by sudden loss of function caused by an abnormality in the blood supply to the brain. Stroke presents with different levels of severity ranging from "transient ischemic attack" or "TIA" (no permanent disability), to "partial nonprogressing stroke" (persistent but no calamitous damage), to "complete stroke" (permanent, calamitous neurological deficit). Mini or micro-stroke refers to sudden loss of blood supply to cells in the CNS, including the retina. In some cases, mini or microstrokes can not be detected by standard imaging techniques (e.g. Magnetic Imaging Resonance, MRI). "Silent" strokes that occur in smaller blood vessels in the brain that become blocked or rupture. Silent or micro/mini strokes are unlikely to involve classic stroke symptoms, such as headache, dizziness or loss of motor skills. Silent and/or micro/mini strokes may increase the risk of future major strokes and may be associated with cognitive abnormalities, such as dementia. Ischemia (diminished or stopped blood flow) and infarction (cell damage and death within the zone of ischemia) are the pathologic processes in stroke that lead to neurologic deficits. "Ischemic stroke" is caused by an obstruction of blood vessels supplying the brain. The primary subcategories of ischemic stroke are thrombotic stroke, embolic stroke and lacunar infarctions. "Hemorrhagic stroke" is caused by the rupture of blood vessels supplying blood to the brain. The primary subcategories of hemorrhagic stroke are subarachnoid hemorrhage (SAH) and intracerebral hemorrhage (ICH).

The term "focal cerebral ischemia" as used herein in reference to the central nervous system, is meant the condition that results from the blockage of a single artery that supplies blood to the brain or spinal cord, resulting in the death of cellular elements in the territory supplied by that artery.

The term "global cerebral ischemia" generally refers to a pathology in which blood flow to the entire brain is diminished, often caused by cardiac arrest or hypotension, for example. In global cerebral ischemia, cells that are particularly vulnerable to ischemia tend to die or become injured, resulting in patches of damage distributed around the brain. This differs from the type of damage that occurs in focal cerebral ischemia.

The term "ischemic episode" is used to mean any circumstance that results in a deficient supply of blood to a tissue. Cerebral ischemic episodes result from a deficiency in the blood supply to the brain. The spinal cord, which is also a part of the central nervous system, is equally susceptible to ischemia resulting from diminished blood flow. An ischemic episode may be caused by a constriction or obstruction of a blood vessel, as occurs in the case of a thrombus or embolus. Alternatively, the ischemic episode can result from any form of compromised cardiac function, including cardiac arrest.

The term "oxidative associated diseases" generally refers to pathological conditions that result at least in part from the production of or exposure to free radicals, particularly oxyradicals, or reactive oxygen species. It is evident to those of skill in the art that most pathological conditions are multifactorial, and that assigning or identifying the predominant causal factors for any particular condition is frequently difficult. For these reasons, the term "free radical associated disease" encompasses pathological states that are recognized as conditions in which free radicals or ROS contribute to the pathology of the disease, or wherein administration of a free radical inhibitor (e.g. desferroxamine), scavenger (e.g. tocopherol, glutathione) or catalyst (e.g. superoxide dismutase, catalase) is shown to produce detectable benefit by decreasing symptoms, increasing survival, or providing other detectable clinical benefits in treating or preventing the pathological state. For the purpose of the present application, oxidative associated diseases may include, without limitation, free radical associated diseases, such as ischemia, ischemic reperfusion injury, inflammatory diseases, systemic lupus erythematosis, myocardial ischemia or infarction, cerebrovascular accidents (such as a thromboembolic or hemorrhagic stroke) that can lead to ischemia or an infarct in the brain, operative ischemia, traumatic hemorrhage (for example a hypovolemic stroke that can lead to CNS hypoxia or anoxia), spinal cord trauma, Down's syndrome, Crohn's disease, autoimmune diseases (e.g. rheumatoid arthritis or diabetes), cataract formation, uveitis, emphysema, gastric ulcers, oxygen toxicity, neoplasia, undesired cellular apoptosis, radiation sickness, and others. The present invention is believed to be particularly beneficial in the treatment of oxidative associated diseases of the CNS. In particular embodiments, the pharmaceutical composition of the present invention is used for preventing, arresting, or treating neurological damage in Parkinson's disease, ageing, Alzheimer's disease and HIV dementia; autoimmune neurodegeneration of the type that can occur in encephalitis, and hypoxic or anoxic neuronal damage that can result from apnea, ageing, respiratory arrest or cardiac arrest, and anoxia caused by drowning, brain surgery or trauma (such as concussion or spinal cord shock).

Many biochemical events surround neuronal damage, particularly as may occur in the brain as a result of cerebral ischemia, trauma, or degeneration. For example, parts of the brain may be damaged as the result of deprivation of blood flow during and after what is commonly referred to as "stroke." This condition (focal ischemia) may occur when one or more of the cerebral arteries is occluded by a thromboembolus or when there is a hemorrhage of one or more of the cerebral arteries. The brain, as well as other parts of the central nervous system, can also be damaged when deprived of blood flow as a result of cardiac arrest (global ischemia). Other sources of damage to central nervous tissue include, but are not limited to, concussive trauma to the brain or spinal cord, and degenerative conditions, such as Alzheimer's disease, or loss of neural function during ageing. Methods described herein can be used in the diagnosis and/or treatment of any conditions that include damage of neural tissue. The invention should not be limited to the conditions mentioned above or exemplified below.

Depending on its duration, cessation of blood flow to all or part of the central nervous system (CNS) results in neuronal death in the affected areas. In the case of focal ischemia, cell death will center in the region deprived of blood; in the case of global ischemia, cell death may be focused in those areas of the brain that are most susceptible or vulnerable to insult.

The present invention provides a treatment method for brain injury, including oxidative damage to neurons and glial cells, and for promoting neuroprotective responses of astrocytes in response to oxidative stress and/or brain injury. In an embodiment, methods for treating oxidative damage to astrocytes and promoting neuroprotective responses may include administering to a subject a pharmaceutical composition comprising a therapeutically effective amount of at least one P2Y receptor ligand. The term "therapeutically effective amount," as used herein, generally means an amount effective to promote or stimulate the neuroprotective function of astrocytes, which is an amount effective to reverse, halt, or delay damage to astrocytes that is associated with oxidative stress (e.g., ROS), or to confer protection of neurons from subsequent damage and degeneration. Pharmacologically, the term may also mean an amount sufficient to initiate $IP_3$-mediated intracellular $Ca^{2+}$ release and $Ca^{2+}$-dependent mitochondrial metabolism in affected astrocytes. In one embodiment, treatment methods may include providing a sufficient amount of a P2Y-R or GPCR agonist to increase the local concentration of said agonist at least in the affected area of the central nervous system. The method administers to a subject an effective amount of P2Y receptor agonist such that the extracellular concentration of the agonist is sufficient to activate the P2Y receptors on the cell surface of CNS astrocytes.

Disorders amenable to treatment disclosed in this invention include any disorder or pathology in which astrocyte function, in particular neuroprotective function, plays a contributing role. One set of non-limiting embodiments contemplates protecting CNS, in particular cortical, neurons from reperfusion injury resulting from stroke, trauma, post-surgical trauma and complications (such as, e.g., oxidative damage) by stimulating the neuroprotective function of astrocytes with P2Y receptor agonists. Another set of non-limiting embodiments contemplates counteracting the decreased neuroprotective potential of astrocytes during aging or neurodegenerative disorders. Little is known about the cumulative effects of oxidative damage on astrocytes during aging. Degradation of their supportive and neuroprotective functions is likely to contribute to reduced neural function during the aging process. More specifically, the following oxidative associated diseases of the CNS, which are provided by way of non-limiting example only, are well suited to treatment with the presently described methods: stroke, focal cerebral ischemia, global cerebral ischemia, cerebral ischemic episodes, ischemic reperfusion injury, operative ischemia, traumatic hemorrhage (for example a hypovolemic stroke that can lead to CNS hypoxia or anoxia), oxygen toxicity, neurodegenerative damage associated with Parkinson's disease, ageing, Alzheimer's disease and HIV dementia, autoimmune neurodegeneration of the type that can occur in encephalitis, and hypoxic or anoxic neuronal damage that can result from apnea, ageing, respiratory arrest or cardiac arrest, and anoxia caused by drowning, brain surgery or trauma (such as concussion or spinal cord shock).

The present methods can also be used in conjunction with other therapeutic modalities for treating neural degeneration, including but not limited to administration with growth factors, neurotrophins, cytokines, ribozymes, anti-inflammatory agents, antibiotics, anti-viral agents, and gene therapy.

P2Y receptors are localized to multiple cell types in the CNS, in particular astrocytes. Astrocytes play a fundamental role in signaling, maintenance and protection of the brain. Without being bound by any particular theory or mechanism of action, it is Applicant's belief that astrocyte resistance to stress (ischemia, trauma or age-related), and neuroprotection can be enhanced by activation of a GPCR signaling pathway in astrocytes. This enhanced protection pathway is associated with an increase in mitochondrial ATP production in astrocytes. GPCR-enhanced astrocyte function and neuroprotection, as described herein, appears to be associated with $IP_3$-mediated increases in cytosolic $Ca^{2+}$ which, through the metabotropic inositol triphosphate ($IP_3$) signaling pathway, increase mitochondrial $Ca^{2+}$ and consequently, increase respiration and ATP production. The production of intracellular ATP via $Ca^{2+}$-induced activation of matrix dehydrogenases is very rapid, occurring at levels ten-fold faster than stimulation by feedback from ATP/ADP pools. Evidence disclosed herein indicates that this enhanced neuroprotection depends on astrocyte mitochondrial function.

The present disclosure provides for methods of using a pharmaceutical composition comprising P2Y receptor agonists for purpose of treating oxidative associated diseases of the CNS. P2Y agonists, including analogs, derivatives and pharmaceutically acceptable salts thereof that may find use in the present treatment methods may include, but are not limited to, nucleoside mono-, di-, and triphosphates and dinucleoside polyphosphates. Nucleoside monophosphates useful for the present purposes may include adenosine 5'-monophosphate (AMP) and its derivatives such as 2-thio-ether-substituted AMP, e.g., 2-hexylthio AMP. Nucleoside di- and triphosphates useful in this application may include uridine 5'-di- and triphosphate (UDP and UTP) and their analogs of general formulae Ia and Ib; adenosine 5'-di- and triphosphate (ADP and ATP) and their analogs of general formulae IIa and IIb; and cytosine 5'-di- and triphosphate (CDP and CTP) and their analogs of general formulae IIIa and IIIb; and dinucleoside polyphosphates of general formula IV.

UDP and its analogs are depicted by general formula Ia:

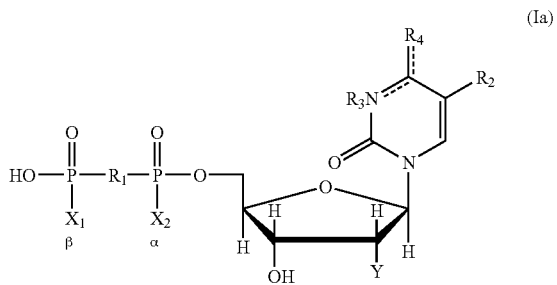

(Ia)

wherein: $X_1$, and $X_2$ are each independently either —OH, —O⁻, —SH, or —S⁻; Y is H or OH; $R_1$ is selected from the group consisting of O, imido, methylene, and dihalomethylene (e.g., dichloromethylene, difluoromethylene); $R_2$ is selected from the group consisting of H, halogen, alkyl, substituted alkyl, alkoxyl, nitro and azido; $R_3$ is selected from the group consisting of nothing, H, alkyl, acyl (including arylacyl), and arylalkyl; and $R_4$ is selected from the group consisting of —OR', —SR', NR', and NR'R", wherein R' and R" are independently selected from the group consisting of H, alkyl, substituted alkyl, aryl, substituted aryl, arylalkyl, alkoxyl, and aryloxyl, and with the proviso that R' is absent when $R^4$ is double bonded from an oxygen or sulfur atom to the carbon at the 4-position of the pyrimidine ring.

As used herein, the term "alkyl" generally refers to $C_{1-10}$ inclusive, linear, branched, or cyclic, saturated or unsaturated (i.e., alkenyl and alkynyl)hydrocarbon chains, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, allenyl and optionally substituted arylalkenyl and arylalkyny groups. As used herein, the term "acyl" refers to an organic acid group wherein the —OH of the carboxyl group has been replaced with another substituent (i.e., as represented by RCO—, wherein R is an alkyl or an aryl group). As such, the term "acyl" specifically includes arylacyl groups. Specific examples of acyl groups include acetyl and benzoyl. As used herein, the term "aryl" refers to 5 and 6-membered hydrocarbon and heterocyclic aromatic rings. Examples of aryl groups include cyclopentadienyl, phenyl, furan, thiophene, pyrrole, pyran, pyridine, imidazole, isothiazole, isoxazole, pyrazole, pyrazine, pyrimidine, and the like. The term "alkoxyl" as used herein refers to $C_{1-10}$ inclusive, linear, branched, or cyclic, saturated or unsaturated oxo-hydrocarbon chains, including for example methoxy, ethoxy, propoxy, isopropoxy, butoxy, t-butoxy, and pentoxy. The term "aryloxyl" as used herein refers to aryloxy such as phenyloxyl, and alkyl, halo, or alkoxyl substituted aryloxyl. As used herein, the terms "substituted alkyl" and "substituted aryl" include alkyl and aryl groups, as defined herein, in which one or more atoms or functional groups of the aryl or alkyl group are replaced with another atom or functional group, for example, halogen, aryl, alkyl, alkoxy, hydroxy, nitro, amino, alkylamino, dialkylamino, sulfate, and mercapto. The terms "halo," "halide," or "halogen" as used herein refer to fluoro, chloro, bromo, and iodo groups.

Compounds illustrative of the compounds of Formula (Ia) may include, though are not limited to: uridine 5'-diphosphate (UDP); uridine 5'-O-(2-thiodiphosphate)(UDPβS); 5-bromouridine 5'-diphosphate (5-BrUDP); 5-(1-phenylethynyl)-uridine 5'-diphosphate (5-(1-phenylethynyl)UDP); 5-methyluridine 5'-diphosphate (5-methylUDP); 4-hexylthiouridine 5'-diphosphate (4-hexylthioUDP); 4-mercaptouridine 5'-diphosphate (4-mercaptoUDP); 4-methoxyuridine 5'-diphosphate (4-methoxyUDP); 4-(N-morpholino)uridine 5'-diphosphate (4-(N-morpholino)UDP; 4-hexyloxyuridine 5'-diphosphate (4-hexyloxyUDP); N,N-dimethylcytidine 5'-diphosphate (N,N-dimethylCDP); N-hexylcytidine 5'-diphosphate (N-hexylCDP); and N-cyclopentylcytidine 5'-diphosphate (N-cyclopentylCDP).

Preferred compounds of Formula Ia may include UDP and UDPβS and 4-thio UDP. Certain compounds of Formula Ia (e.g., UDP, dUDP, UDPβS, and 4-mercaptoUDP) are known and may be made in accordance with known procedures or variations thereof, which will be apparent to those skilled in the art. For example, the identification and preparation of certain thiophosphate analogues of nucleoside diphosphates (such as UTPβS) are set forth in U.S. Pat. No. 3,846,402 (Eckstein et al.), and in R. S. Goody and F. Eckstein, J. Am. Chem. Soc. 93: 6252-6257 (1971). Alternatively, UDP, and other analogs thereof are also commercially available from vendors such as Sigma (St. Louis, Mo.) and Pharmacia (Uppsala, Sweden).

UTP and its analogs are depicted by general formula Ib;

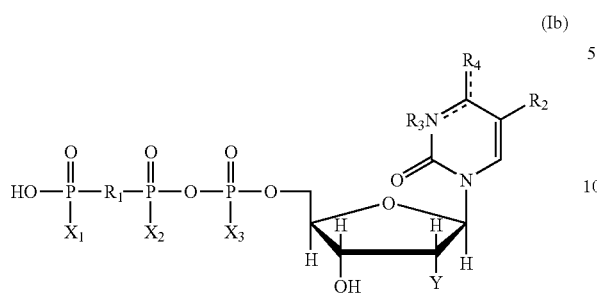

(Ib)

wherein: $X_1$, $X_2$ and $X_3$ are each independently either —OH, —O⁻, —SH, or —S⁻, Y is H or OH; $R_1$, $R_2$, $R_3$ and $R_4$ are defined as above in Formula Ia. Preferably, $X_2$ and $X_3$ are O—, $R_1$ is oxygen or imido, and $R_2$ is H. Particularly preferred compounds of Formula Ib may include uridine 5'-triphosphate (UTP) and uridine 5'-O-(3-thiotriphosphate) (UTPγS).

ADP and its analogs are depicted by general Formula IIa:

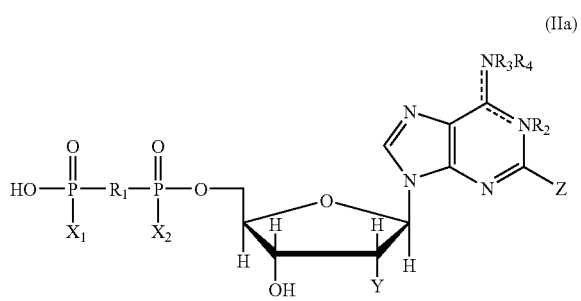

(IIa)

wherein: $R_1$, $X_1$, $X_2$ and Y are defined as in Formula Ia; Z is H, Cl, or SR, wherein R is alkyl ($C_1$-$C_{20}$, saturated or unsaturated); $R_3$ and $R_4$ are H while $R_2$ is nothing and there is a double bond between N-1 and C-6 (adenine), or $R_3$ and $R_4$ are H while $R_2$ is nothing and Z is SR, or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,$N^6$-ethenoadenine). Particularly preferred compounds of Formula IIa may include 5'-adenosine diphosphate (ADP), 2-methyl-SADP and N-methanocarba-2MeSADP ("MRS2365").

ATP and its analogs are depicted by general formula IIb:

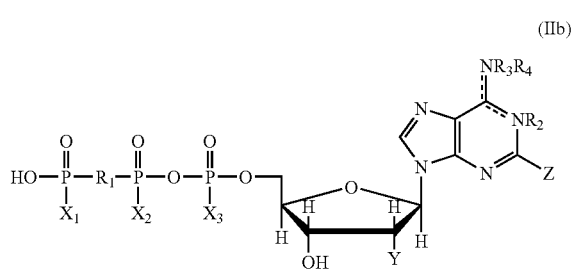

(IIb)

wherein: $R_1$, $X_1$, $X_2$, $X_3$ and Y are defined as in Formula Ib, and $R_2$, $R_3$, $R_4$ and Z are defined as in Formula IIa.

CDP and its analogs are depicted by general Formula IIIa:

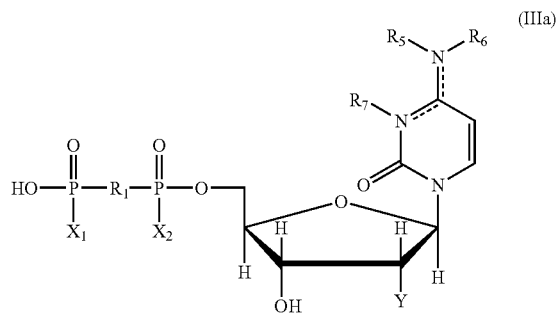

(IIIa)

wherein: $R_1$, $X_1$, $X_2$ and Y are defined as in Formula Ia; $R_5$ and $R_6$ are H while $R_7$ is nothing and there is a double bond between N-3 and C-4 (cytosine), or $R_5$, $R_6$ and $R_7$ taken together are —CH=CH—, forming a ring from N-3 to N-4 with a double bond between N-4 and C-4 (3,$N^4$-ethenocytosine), optionally the hydrogen of the 4- or 5-position of the etheno ring is substituted with alkyl, substituted alkyl, aryl; substituted aryl (heteroaryl, etc.), alkoxyl, nitro, halogen, or azido.

CTP and its analogs are depicted by general Formula IIIb:

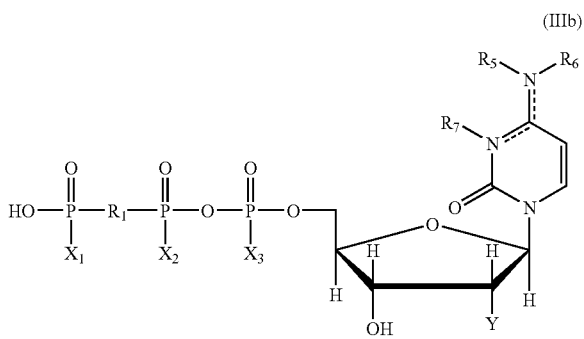

(IIIb)

wherein: $R_1$, $X_1$, $X_2$, $X_3$ and Y are defined as in Formula Ib, and $R_5$, $R_6$ and $R_7$ are defined as in Formula IIIa. Preferred compounds of Formula IIIb may include cytidine 5'-triphosphate (CTP) and 4-nitrophenyl ethenocytidine 5'-triphosphate.

For simplicity, Formulas I, II, and III, herein illustrate the active compounds in the naturally occurring D-configuration, but it is to be understood that, unless otherwise indicated, the present disclosure also encompasses compounds in the L-configuration, and mixtures of compounds in the D- and L-configurations.

Dinucleoside polyphosphates are depicted by general Formula IV:

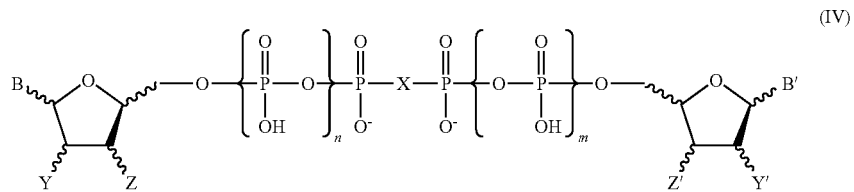

(IV)

wherein: X is oxygen, methylene, difluoromethylene, imido; n=0, 1 or 2; m=0, 1 or 2; n+m=0, 1, 2, 3 or 4; B and B' are each independently a purine residue or a pyrimidine residue linked through the 9- or 1-position, respectively; Z=OH or N₃; Z'=OH or N₃; Y=H or OH; and Y'=H or OH. The ribosyl moieties are in the D configuration, as shown, but may be L-, or D- and L-.

A preferred compound of Formula IV includes Formula IVa:

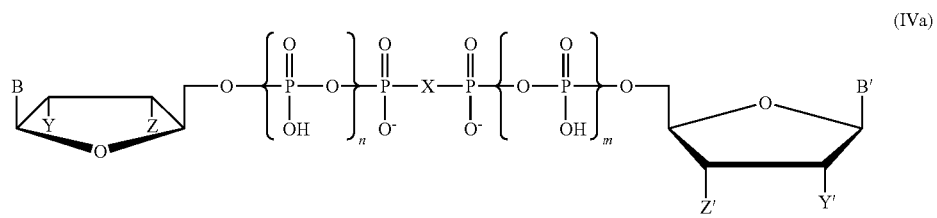

(IVa)

wherein: X=O; n+m=1 or 2; Z, Z', Y and Y'=OH; B and B' are uracil, thymine, cytosine, guanine, adenine, xanthine, hypoxanthine or as defined in Formulas V and VI; or X=O; n+m=3 or 4; Z, Z', Y and Y'=OH; B=uracil; B' is uracil, thymine, cytosine, guanine, adenine, xanthine, hypoxanthine or as defined in Formulas V and VI; or X=O; n+m=1 or 2; Z, Y and Z'=OH; Y'=H; B=uracil; B' is uracil, thymine, cytosine, guanine, adenine, xanthine, hypoxanthine or as defined in Formulas V and VI; or X=O; n+m=0, 1 or 2; Z and Y=OH; Z'=N₃; Y'=H; B=uracil; B'=thymine; or X=O; n+m=0, 1 or 2; Z and Z'=N₃; Y and Y'=H; B and B'=thymine; or X=CH₂, CF₂ or NH; n and m=1; Z, Z', Y and Y'=OH; B and B' are uracil, thymine, cytosine, guanine, adenine, xanthine, hypoxanthine or as defined in Formulas V and VI:

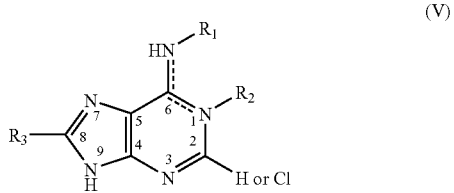

(V)

wherein $R_1$ is hydrogen, $C_{1-8}$ alkyl, $C_{3-6}$ cycloalkyl, phenyl, or phenyloxy; wherein at least one hydrogen of said $C_{1-8}$ alkyl, phenyl, phenyloxy, is optionally substituted with a moiety selected from the group consisting of halogen, hydroxy, $C_{1-4}$ alkoxy, $C_{1-4}$ alkyl, $C_{6-10}$ aryl, carboxy, cyano, nitro, sulfonamido, sulfonate, phosphate, sulfonic acid, amino, $C_{1-4}$ alkylamino, di-$C_{1-4}$ alkylamino wherein said alkyl groups are optionally linked to form a heterocycle, ω-A(alkyl)CONH(alkyl)-, and ω-A(alkyl)NHCO(alkyl)-, wherein A is amino, mercapto, hydroxy or carboxyl; $R_2$ is 0 or is absent; or $R_1$ and $R_2$ taken together form a 5-membered fused imidazole ring optionally substituted on the 4- or 5-positions of the etheno moiety with $C_{1-4}$ alkyl, phenyl or phenyloxy, wherein at least one hydrogen of said $C_{1-4}$ alkyl, phenyl, phenyloxy, is optionally substituted with a moiety selected from the group consisting of halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di-$C_4$ alkylamino wherein said dialkyl groups are optionally linked to form a heterocycle; and $R_3$ is hydrogen, NH₂, $C_{1-8}$ alkyl, $C_{3-6}$ cycloalkyl, phenyl; or phenyloxy; wherein at least one hydrogen of said NH₂, $C_{1-8}$ alkyl, phenyl, or phenyloxy, is optionally substituted with a moiety selected from the group consisting of halogen, hydroxy, $C_{1-4}$ alkyl, $C_{6-10}$ aryl, $C_{7-12}$ arylalkyl, $C_{1-4}$ alkoxy, $C_{7-12}$ arylalkyloxy, $C_{1-4}$ alkylthio, phenylthio, $C_{7-12}$ arylalkylthio, carboxy, cyano, nitro, sulfonamido, sulfonate, phosphate, sulfonic acid, amino, $C_{1-4}$ alkylamino, phenylamino, $C_{7-12}$ arylalkyamino, di-$C_{1-4}$ alkyl amino wherein said dialkyl groups are optionally linked to form a heterocycle, ω-A(alkyl)CONH(alkyl)B-, and ω-A(alkyl)NHCO(alkyl)B-, wherein A and B are independently amino, mercapto, hydroxy or carboxyl.

The substituted derivatives of adenine (Formula V) may include adenine 1-oxide; 1,N6-(4- or 5-substituted etheno) adenine; 6-substituted adenine; or 8-substituted aminoadenine, [6-aminohexyl]carbamoylmethyl-ade-nine; and ω-acylated-amino(hydroxy, thiol and carboxy)alkyl($C_{2-10}$)-adenine, wherein the acyl group is chosen from among, but not limited to, acetyl, trifluororoacetyl, benzoyl, substituted-benzoyl, etc., or the carboxylic moiety is present as its ester or amide derivative, for example, the ethyl or methyl ester or its methyl, ethyl or benzamido derivative.

B and B', can also be a pyrimidine with the general formula of Formula VI, linked through the 1-position to ribosyl residue:

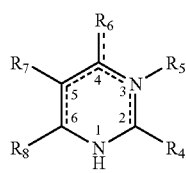

(VI)

wherein: $R^4$ is hydrogen, hydroxy, mercapto, amino, cyano, $C_{7-12}$ arylalkoxy, $C_{1-6}$ alkylthio, $C_{1-6}$ alkoxy, $C_{1-6}$ alkylamino or $diC_{1-4}$ alkylamino, wherein the alkyl groups are optionally linked to form a heterocycle; R is hydrogen, acetyl, benzoyl, $C_{1-6}$ alkyl, phenyloxy, $C_{1-5}$ alkanoyl, aroyl, or sulphonate; $R_6$ is hydroxy, mercapto, $C_{1-4}$ alkoxy, $C_{7-12}$ arylalkoxy, $C_{1-6}$ alkylthio, amino, S-phenyl, $C_{1-5}$ disubstituted amino, triazolyl, $C_{1-6}$ alkylamino, or di-$C_{1-4}$ alkylamino wherein said dialkyl groups are optionally linked to form a heterocycle or linked to $N_3$ to form a substituted ring; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl; phenyl; or phenyloxy; wherein at least one hydrogen of said $C_{1-4}$ alkyl; phenyl or phenyloxy is optionally substituted with a moiety selected from the group consisting of halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di $C_{1-4}$ alkylamino wherein said dialkyl groups are optionally linked to form a heterocycle; $R_7$ is hydrogen, hydroxy, cyano, nitro, or $C_{2-8}$ alkenyl; wherein said alkenyl moiety is optionally linked through an oxygen to form a ring, wherein at least one hydrogen of said alkenyl moiety on the carbon adjacent to said oxygen is optionally substituted with $C_{1-6}$ alkyl, phenyl, substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, or propenoic acid; or $R_6$ and $R_7$ together form a 5 or 6-membered saturated or unsaturated ring bonded through N or O at $R_6$, such ring optionally contains substituents that themselves contain functionalities; provided that when $R_8$ is amino or substituted amino, $R_7$ is hydrogen; and $R_8$ is hydrogen, amino or di-$C_{1-4}$ alkylamino, $C_{1-4}$ alkoxy, $C_{7-12}$ arylalkoxy, $C_{1-4}$ alkylthio, $C_{7-12}$ arylalkylthio, carboxamidomethyl, carboxymethyl, methoxy, methylthio, phenoxy or phenylthio.

In the general structure of Formulae I, II, III, V, and VI above, the dotted lines in the 2- to 6-positions are intended to indicate the presence of single or double bonds in these positions; the relative positions of the double or single bonds being determined by whether the $R_4$, $R_5$ and $R_6$ substituents are capable of keto-enol tautomerism.

In the general structures of Formula V and VI above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

Preferred dinucleoside polyphosphate compounds useful in this invention are $P^1$, $P^4$-di (uridine-5')-tetraphosphate, $dUP_4U$, $U_2P_3$, $U_2P_5$, $dCP_4U$, $CP_4U$, IP51, $AP_4A$, $CP_3U$, $UP_3A$ and $A^2P^3$.

Some compounds of Formula I, II and III can be made by methods known those skilled in the art; some compounds are commercially available, for example, from Sigma Chemical Co. (St. Louis, Mo. 63178). Compounds of Formulae Ia (UDP and its analogs) can be prepared according to WO 99/09998. Compounds of Formulae Ib, IIb and IIIb (UTP, ATP, CTP and their analogs) can be prepared according to U.S. Pat. No. 5,763,447. Compounds of Formula IV can be made in accordance with known procedures described by Zamecnik, et al., Proc. Natl. Acad. Sci. USA 89, 838-42 (1981); and Ng and Orgel, Nucleic Acids Res. 15:3572-80 (1987), Pendergast et al., U.S. Pat. No. 5,837,861, or variations thereof.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4+$ (wherein X is $C_{1-4}$). Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies that may be employed to prepare non-toxic pharmaceutically acceptable salts and acylated prodrugs of the compounds.

Dosage and Administration

The P2Y-R or GPCR agonist may be administered to a subject at a dosage level up to conventional dosage levels for such compounds but will typically be less than about 2 gm per day. Suitable dosage levels may depend upon the overall systemic effect of the chosen P2Y-R or GPCR agonist, but typically suitable levels will be about 0.001 to 50 mg/kg body weight of the patient per day, from about 0.005 to 30 mg/kg per day, or from about 0.05 to 10 mg/kg per day. The compound may be administered on a regimen of up to 6 times per day, between about 1 to 4 times per day, or once per day.

In the case where an oral composition is employed, a suitable dosage range is, e.g. from about 0.01 mg to about 100 mg of a P2Y-R or GPCR agonist per kg of body weight per day, preferably from about 0.1 mg to about 10 mg per kg and for cytoprotective use from 0.1 mg to about 100 mg of a P2Y-R or GPCR agonist per kg of body weight per day.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skill level of a clinician.

In some embodiments, compositions may include all compositions of 1.0 gram or less of a particular P2Y-R or GPCR agonist, in combination with 1.0 gram or less of one or more other P2Y-R or GPCR agonist, in an amount which is effective to achieve its intended purpose. While individual subject needs vary, determination of optimal ranges of effective amounts of each component is with the skill of the art. Typically, P2Y-R or GPCR agonist may be administered to mammals, in particular humans, orally at a dose of 5 to 100 mg per day referenced to the body weight of the mammal or human being treated for a particular disease. Typically, a structural carotenoid analog or derivative or synthetic intermediate may be administered to mammals, in particular humans, parenterally at a dose of between 5 to 1000 mg per day referenced to the body weight of the mammal or human being treated for a particular disease. In other embodiments, about 100 mg of a structural carotenoid analog or derivative or synthetic intermediate is either orally or parenterally administered to treat or prevent disease.

The unit oral dose may comprise from about 0.25 mg to about 1.0 gram, or about 5 to 25 mg, of a P2Y-R or GPCR agonist. The unit parenteral dose may include from about 25 mg to 1.0 gram, or between 25 mg and 500 mg, of a P2Y-R or GPCR agonist. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a P2Y-R or GPCR agonist as a raw chemical, the compounds may be administered as part of a pharmaceutical preparation containing suitable pharmaceutically acceptable carriers, preservatives, excipients and auxiliaries which facilitate processing of the structural carotenoid analog or derivative or synthetic intermediates which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

In some embodiments in which one or more additional medicaments or compositions suitable for the treatment of oxidative, trauma or age-associated diseases of the CNS in a subject may be administered in conjunction with a P2Y-R or GPCR agonist. In an embodiment, a P2Y-R or GPCR agonist in combination with the one or more additional medicaments may be administered separately in separate dosage forms or together in a single unit dosage form. Where separate dosage formulations are used, the P2Y-R or GPCR agonist and one or more additional medicaments or compositions may be administered at substantially the same time, i.e., concurrently, or at separately staggered times, i.e., sequentially, and in any order. In certain embodiments the P2Y-R or GPCR agonist and the one or more additional medicaments or compositions may be co-administered concurrently on a once-a-day (QD) dosing schedule; however, varying dosing schedules, such as administering the P2Y-R or GPCR agonist once per day and the one or more additional medicaments or compositions once, twice or more times per day, or the one or more additional medicaments or compositions once per day and the P2Y-R or GPCR agonist once, twice or more times per day, is also encompassed herein. According to certain application(s) of the present embodiments, a single oral dosage formulation comprising the P2Y-R or GPCR agonist and the optional one or more additional medicaments or compositions may be preferred. In other embodiments, it may be desirable to administer the P2Y-R or GPCR agonist separately from the one or more additional medicaments or compositions. A single dosage formulation will provide convenience for the patient.

The one or more additional medicaments or compositions suitable for the treatment of oxidative associated diseases of the CNS in a subject may be administered at a dosage level up to conventional dosage levels for such compounds. Suitable dosage levels will depend upon the effect and the pharmacological properties of the chosen additional medicaments or compositions, but typically suitable levels will be between about 0.001 to 50 mg/kg body weight of the patient per day, between about 0.005 to 30 mg/kg per day, or between about 0.05 to 10 mg/kg per day. In some embodiments, the compound may be administered on a regimen of up to 6 times per day, from 1 to 4 times per day, or once per day.

In the case where an oral composition is employed, an exemplary dosage range is, e.g. from about 0.01 mg to about 100 mg of each additional medicament or composition per kg of body weight per day, or from about 0.1 mg to about 10 mg per kg of each additional medicament or composition per kg of body weight per day.

With respect to treatment associated with brain injury, the compound can be administered before, during or after the injurious event. In some embodiments, it is appreciated that the compound can be administered up to 2 hours following the event, although the compound is preferably still efficacious when administered 6, 12, 18 or even 24 hours following the injury. In embodiments requiring rapid treatment and response, the compound can be administered by any of a number of parenteral routes, including intravenous, intraarterial, intrathecal, intranasal, intracerebroventricular and the like. It is appreciated that the compound is able to cross the damaged blood brain barrier after brain injury.

In the case of oxidative stress arising from brain injury, administration of P2Y-R or GPCR agonists to a subject in accordance with the treatment methods described herein will be most effective when administered to the subject as early as possible following the injurious event. In an embodiment, a P2Y-R or GPCR agonist will ideally be administered to a subject within about 2 hours of the neural injury occurring. In a preferred embodiment, a P2Y-R or GPCR agonist may be administered to a subject within about 30 minutes of the neural injury occurring.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, $8^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, New York, 2001).

Pharmaceutical Compositions

Any suitable route of administration may be employed for providing a patient with an effective dosage of drugs of the present invention. For example, oral, rectal, topical, parenteral, ocular, intracranial, pulmonary, nasal, and the like may be employed. Dosage forms may include tablets, troches, dispersions, suspensions, solutions, capsules, creams, ointments, aerosols, and the like. In certain embodiments, it may be advantageous that the compositions described herein be administered orally. In other embodiments, it may be advantageous that the compositions described herein be administered parenterally. In yet other embodiments, it may be advantageous that the compositions described herein be administered locally, at the site of tissue injury.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well known in the art of pharmacy.

For administration by inhalation, the drugs used in the present invention are conveniently delivered in the form of an aerosol spray presentation from pressurized packs or nebulisers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropyl-methyl-cellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian may determine and prescribe the effective amount of the drug required to prevent, counter, or arrest the progress or the development prostate cancer in a subject.

By way of general guidance, the daily oral dosage of each active ingredient, when used for the indicated effects, will range between about 0.001 to 1000 mg/kg of body weight, between about 0.01 to 100 mg/kg of body weight per day, or between about 1.0 to 20 mg/kg/day. Intravenously administered doses may range from about 1 to about 10 mg/kg/minute during a constant rate infusion. Compounds of this invention may be administered in a single daily dose, or the total daily dosage may be administered in divided doses of two, three, or four or more times daily.

The pharmaceutical compositions described herein may further be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

For instance, for oral administration in the form of a tablet or capsule, the pharmacologically active component may be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams or more of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

In an embodiment, the pharmaceutical compositions can be administered locally to the site of neural injury such as by local injection, a minimally invasive drug delivery system, or during a surgical procedure. Alternatively, in some embodiments it may be preferable to administer the composition systemically (such as e.g., by oral or parenteral delivery) such that the localized concentration of a P2Y-R or GPCR agonist in the CNS is sufficient to activate P2Y-R or GPCR present on the surface of astrocytes.

In an embodiment, a P2Y-R or GPCR agonist compound capable of crossing the BBB may be preferred for use in applications in which the integrity of the BBB is not substantially compromised. Examples of such applications include prophylactic administration of the compound, or administration of the compound over time to stimulate neuroprotective response in astrocytes. In certain embodiments however, the selection of a BBB-permeant compound for inclusion in a composition is less crucial and possibly advantageous. For example, in certain types of neural injury (e.g., stroke), there is a transient loss of BBB function that typically occurs within minutes or hours of the event. Consequently, a P2Y-R or GPCR agonist is only exposed to the damaged region of the brain.

In an embodiment, a minimally invasive neural drug delivery system, such as the system disclosed in U.S. Patent Appl. Publ. No. 2004/0243101, can be used to deliver an effective amount of the active compounds to CNS astrocytes with negligible systemic absorption.

The active compounds may be administered to the patient systemically. The term systemic as used herein includes subcutaneous injection; intravenous, intramuscular, intraestemal injection; infusion; inhalation, transdermal administration, oral administration; and intra-operative instillation. It should be noted that in cases of neural injury, the blood-brain barrier (BBB) is typically compromised. Thus, in cases of neural injury, systemically administered compounds are not excluded from the CNS.

One systemic method involves an aerosol suspension of respirable particles comprising the active compound, which the subject inhales. The active compound would be absorbed into the bloodstream via the lungs, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the CNS subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

The active compounds may also be systemically administered to CNS through absorption by the skin using transdermal patches or pads. The active compounds are absorbed into the bloodstream through the skin. Plasma concentration of the active compounds can be controlled by using patches containing different concentrations of active compounds.

Other methods of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs. Additional means of systemic administration of the active compound to the CNS of the subject may involve a suppository form of the active compound, such that a therapeutically effective amount of the compound reaches the eyes via systemic absorption and circulation.

Further means of systemic administration of the active compound involve direct intra-operative instillation of a gel, cream, or liquid suspension form of a therapeutically effective amount of the active compound.

For topical application, the solution containing the active compound may contain a physiologically compatible vehicle, as those skilled in the art can select, using conventional criteria. The vehicles may be selected from the known pharmaceutical vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

For systemic administration such as injection and infusion, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The pharmaceutical activity of P2Y agonist compounds of this invention may be assessed using any of the methods for P2Y activity shown below.

The present invention provides that activation of P2Y purinergic receptors in astrocytes by agonists enhances the survival of neurons in vivo. The present invention describes the utility of agonist-induced activation of purinergic receptors in astrocytes of the CNS in mounting a neuroprotective response by addressing a plurality of diseases under which a therapeutic modality is clinically beneficial.

The invention is illustrated further by the following examples which are not to be construed as limiting the invention in scope or spirit to the specific procedures described in them.

Having now described the invention, the same will be more readily understood through reference to the following example(s), which are provided by way of illustration, and are not intended to be limiting of the present invention.

EXAMPLES

Materials and Methods
Isolation, Culture and Growth of Astrocytes and Neurons

Primary cultures of astrocytes were prepared as previously published (Lin et al., 2005). C57BL/6 male mice were purchased from the National Institute of Aging and maintained in standard accredited housing conditions at the University of Texas Health Science Center Animal Facility. Animal protocols were approved by our Institutional Animal Care Use Committee. Astrocytes were cultured in DMEM F-12 media (Invitrogen, # 11039-021) supplemented with 2 mM glutamine, nonessential amino acids, 10% fetal calf serum, 100 U/ml penicillin/streptomycin (Cambrex BioScience Walkersville, #17-602E) and 1% fungizone (Invitrogen, #15290-018) at 37° C. in an atmosphere containing 5% $CO_2$. The culture medium was changed every 3-5 days. Confluent cells were gently removed by a trypsin EDTA solution and re-plated on 35 mm glass bottom chambers (Bioptechs #04200415C) prior to imaging experiments 3-4 days later. Cells were maintained in plastic culture flasks until the final re-seeding of cells onto a glass bottom chamber and were passed up to 3 times for astrocyte only experiments. For co-culture experiments with neurons, primary astrocytes were plated directly onto corning transwell-clear permeable supports, which physically separates the two cell-types by ~1 mm (# 07-200-170, Fisher scientific). Astrocytes were cultured in transwells until they were ~70% confluent. Mouse cortical neurons (Cambrex Bio Science Walkersville Inc., # M-CX-300) were then cultured onto 6 well mat-tek glass bottom plates and maintained in Neurobasal Medium (Invitrogen, # 21103-049), 2 mM L-Glutamine (Cambrex Bio-Science Walkersville, #17-605E), 100 U/ml penicillin/streptomycin (Cambrex BioScience Walkersville, #17-602E) and B-27 with (Invitrogen, #17504-044) and without antioxidants (Invitrogen, #10889-038), which controls glia contamination to less than 0.5%. The transwell supports with cultured astrocytes were placed in the neuron seeded glass bottom chambers for four days before imaging and both cell types were then maintained in neuronal media. For neuron only experiments, the astrocytes on the transwell supports were removed prior to treatments and imaging.

$O_2$ Consumption Assay $O_2$ consumption was monitored with a Clark electrode (Mitocell S200 micro respirometry system; Strathkelvin Instruments). Astrocytes (500 µl at $10^5$ cells/ml) were loaded into a 500 µl MT200A Respirometer Chamber, suspended by a fixed-speed solid-state magnetic stirrer inside the chamber and maintained at 37° C. by a circulating water bath. $O_2$ was monitored for 4 minutes before injecting 5 µl of ATP (200 µM) into the chamber. $O_2$ consumption was then monitored for another 4 minutes. Changes in $O_2$ levels were calculated by respirometry software. For control recordings, 5 µl of buffer was injected into chamber. Oligomycin astrocytes were treated with oligomycin (0.01 µM) for 30 minutes before trypsinization and loading into chamber.

Intracellular ATP Determination

Intracellular ATP was measured using a luciferin-luciferase kit (Invitrogen, #22066). Plated astrocytes were trypsinized and washed 3× with PBS buffer (GIBCO #14190). An aliquot of cells was set aside to measure the cell density with a hemocytometer. The cells were then suspended in a lysate buffer (4 mM EDTA and 100 mM Tris, pH 7.75) and immediately heated to 100° C. for 5 minutes to minimize enzymatic changes in ATP levels. The supernatant was collected after a 10,000 g centrifugation for 1 minute and used with the luciferin/luciferase kit according to the manufacturer's instructions. Luminescence was measured with a Synergy™ HT Multi-Detection Microplate Reader (BioTek). ATP levels were normalized by cell density.

Imaging Acquisition and Analysis

Mitochondrial membrane potentials ($\Delta\Psi$s) was measured as previously described using the potential sensitive dye tetramethyl rhodamine ethyl ester (TMRE, Molecular Probes, #T-669) (Lin and Lechleiter, 2002). Images were acquired with a 60× oil 1.4 NA objective on a Nikon PCM2000 confocal microscope custom adapted for two-photon imaging. A Ti-sapphire Coherent Mira 900 Laser pumped with a 5W Verdi laser (Coherent Inc., Santa Clara, Calif.) was used to excite TMRE at 800 nm A neutral-density filter wheel was used to attenuate the laser intensity so that no detectable photobleaching of TMRE was observed.

Sensitivity of neurons to oxidative stress was assessed by treating cultures with 100 µM tert-butyl hydrogen peroxide (t-BuOOH, Sigma, #B-2633) for 3 hours. Neurons were then stained with Hoechst 33342 (10 µg/ml, Molecular Probes, #H-3570) to label all cell nuclei and calcein AM (2 µM, #C3100, Molecular Probes, #C3100). Neuronal death was quantified by counting the number of nuclei that did not co-localize with calcien stained cells. Calcein fluorescence is only observed in live cells that have maintained their plasma membrane integrity. Images were acquired on an inverted Nikon TE300 microscope with a Hamamatsu ORCAER camera and Open lab software (Improvision).

$Ca^{2+}$ activity was imaged as previously described (Camacho and Lechleiter, 1995). In brief, cultured astrocytes were incubated with the fura-2 am (Molecular Probes, #F-1221) 30 min prior to the experiment. Images were acquired with two-photon excitation (800 nm) at the rate of 1.5 images/ sec. At this wavelength, only the $Ca^{2+}$ free form of fura-2 is significantly excited. Hence, a $Ca^{2+}$ increase is observed as a decrease in fluorescence. Images were analyzed with Image J and ANALYZE® software (the Mayo Foundation, Rochester, MN). The D-enantiomer of the $1P_3$-BM ester was synthesized by Stuart Conway in the Cambridge University Chemical Laboratory by using a modification of the protocol of Tsien and co-workers (Li et al., 1997).

One-way analysis of variance (ANOVA) was used for all of the data. Differences with a p value<0.05 were considered statistically significant.

Example 1

Extracellular ATP Protects Astrocytes From Oxidative Stress

Figure 1B:
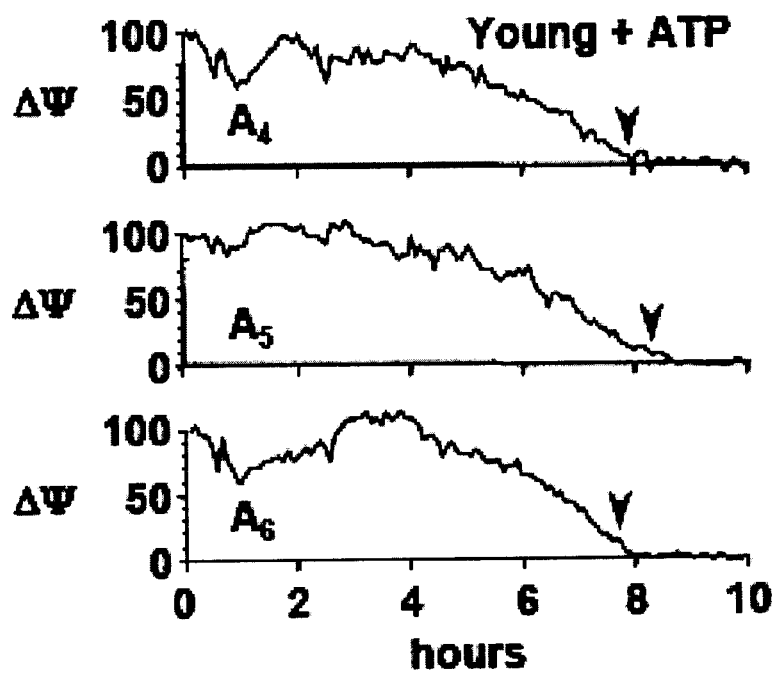
FIG. 1B depicts line plots of the TMRE fluorescence for young astrocytes pre-exposed to extracellular ATP (10 µM) for 10 minutes prior to adding t-buOOH (100 µM) to the perfusate (0 hours)
Figure 1C:
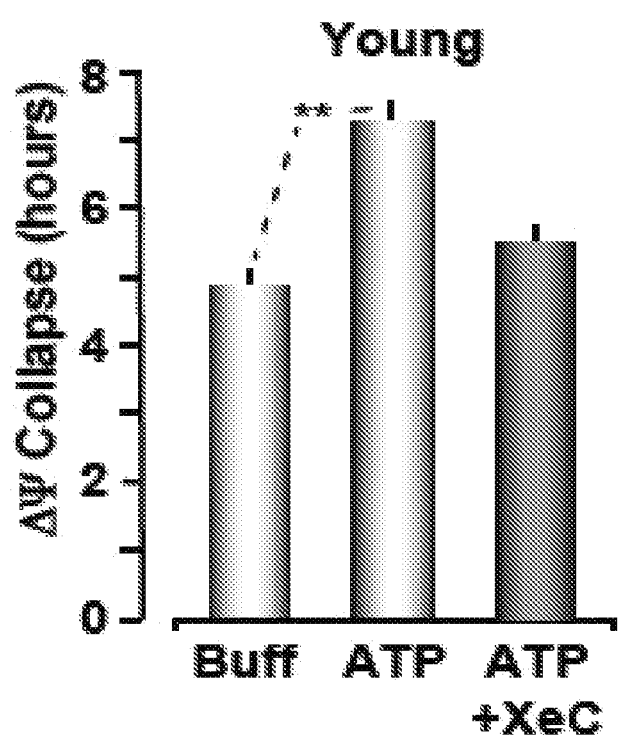
FIG. 1C depicts histograms of the mean times of ΔΨ collapse for young astrocytes exposed to buffer only (Buff), ATP or ATP plus Xestospongin C.
Figure 2A:
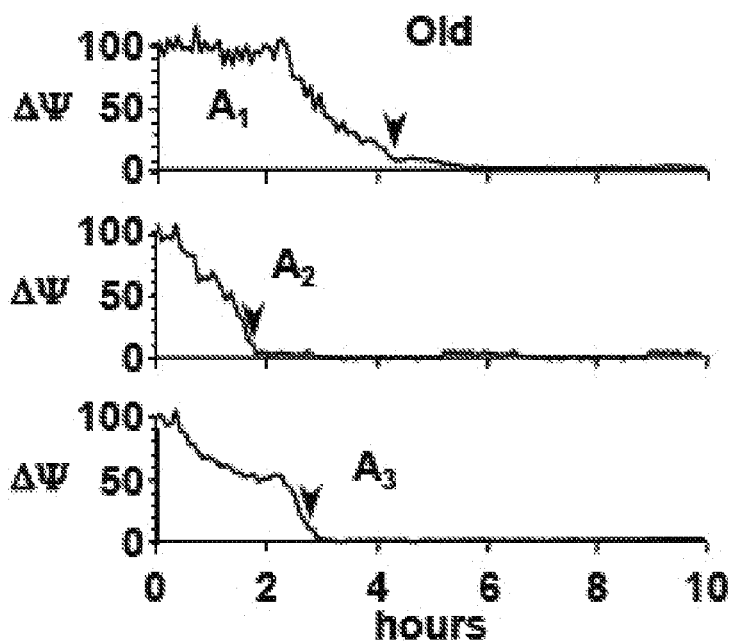
FIG. 2A depicts Intensity line plots of the mean TMRE fluorescence (ΔΨ) for astrocytes cultured from old mice with TMRE labeled mitochondria under oxidative stress for the indicated times.
Figure 2B:
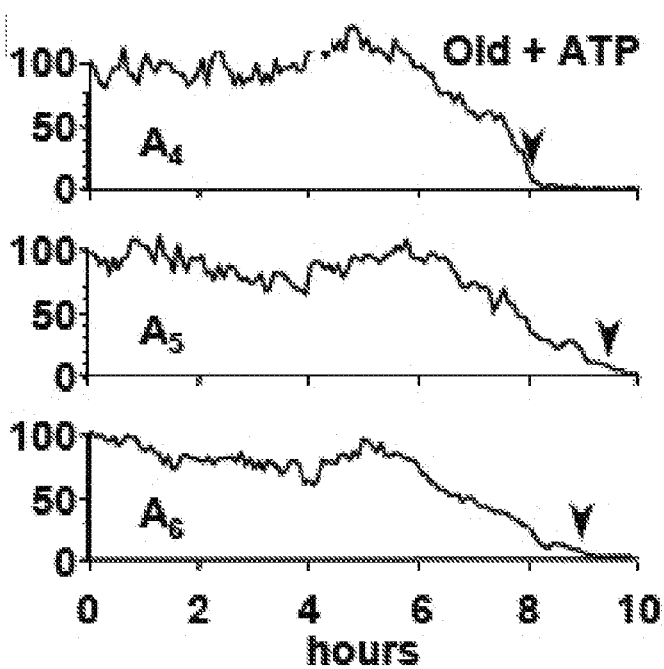
FIG. 2B depicts intensity line plots of TMRE fluorescence for old astrocytes treated with extracellular ATP (10µM) for 10 minutes prior to oxidative stress (t-buOOH, 100µM)
Figure 2C:
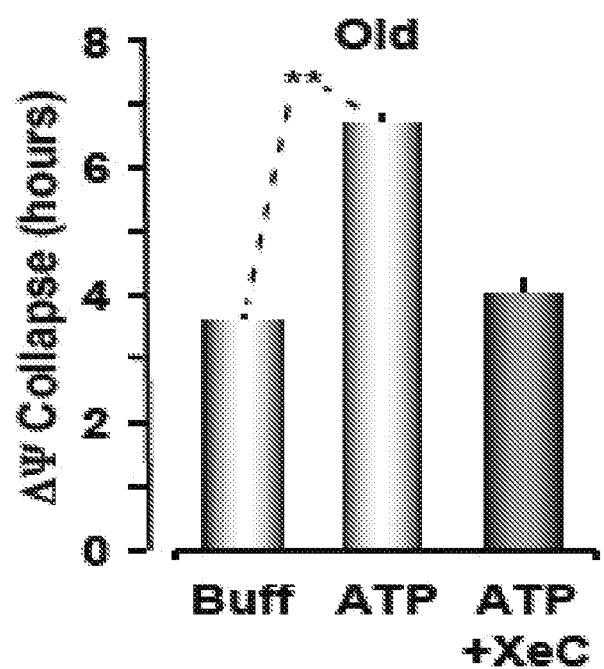
FIG. 2C depicts histograms of the mean times of ΔΨ collapse for old astrocytes exposed to buffer only (Buff), ATP or ATP plus Xestospongin C.

The presence of multiple purinergic receptor isoforms on astrocytes suggests that an increase in extracellular ATP was likely to affect the sensitivity of astrocytes to oxidative stress during the aging process. To investigate this, primary cultures of astrocytes were prepared from the brains of young (4-6 months) and old (26-28 months) mice and re-plated on glass coverslips prior to each imaging experiment as previously described. Seeded glass coverslips were then sealed in an open chamber (Bioptechs Delta T) and perfused at 37° C. with the potential sensitive dye tetramethyl rhodamine ethyl ester (TMRE, 200 nM, Molecular Probes/Invitrogen) to label astrocyte mitochondria. Mitochondrial membrane potentials ($\Delta\Psi$s) were measured every 5 minutes using two-photon microscopy. Each image is a maximum intensity projection of a z-stack of six optical sections (1-$\mu$m steps). Scale bar is 10 $\mu$m. Plated cells were continuously perfused at 37° C. with culture medium containing TMRE (200 nM) and imaged with 2-photon microscopy (800 nm). Oxidative stress was applied to the cells in the perfusate with t-BuOOH (100 $\mu$M). Cell viability was then monitored by the collapse of $\Delta\Psi$ (TMRE fluorescence) to 10% of its initial value. The time course of $\Delta\Psi$ collapse is plotted for 3 astrocytes ($A_1$, $A_2$, $A_3$) in each culture (FIGS. 1B and 2B). Fluorescent units are scaled to 100% at 0 hours. The times when the TMRE fluorescence collapses to 10% of the initial values are indicated by black arrowheads. Histograms of the mean times of $\Delta\Psi$ collapse for young astrocytes exposed to buffer only (Buff), ATP or ATP plus Xestospongin C are depicted in FIG. 1C. The time until $\Delta\Psi$ collapse was significantly faster for old astrocytes (3.62±0.12 h, n=75 cells, pooled from 4 experiments) compared to young astrocytes (4.87±0.48 h, n=15 cells, pooled from 2 experiments). To test the impact of purinergic receptor activation, astrocyte cultures were initially exposed to extracellular ATP (10 $\mu$M) for 10 minutes prior to stressing the cells with t-BuOOH (100 $\mu$M). The perfusate again contained TMRE (200 nM) to monitor $\Delta\Psi$ every five minutes. Under these experimental conditions, it was found that the average time for $\Delta\Psi$ to collapse was significantly increased to 7.35±0.23 h (n=27 cells pooled from 3 experiments, p<0.001) in astrocytes from young mice. Similarly, a ten-minute application of extracellular ATP to astrocytes cultured from old mice significantly increased the average time until $\Delta\Psi$ collapse to 6.65±0.24 h (n=15 cells pooled from 2 experiments, p<0.001) (FIG. 2B). Histograms of the mean times of $\Delta\Psi$ collapse for old astrocytes exposed to buffer only (Buff), ATP or ATP plus Xestospongin C are depicted in FIG. 2C. Remarkably, the collapse time for ATP-treated old astrocytes was significantly greater than non-treated young astrocytes during oxidative stress (p<0.001, FIGS. 1C and 2C). We concluded from these data that a brief application of extracellular ATP to astrocytes established a prolonged period of protection against oxidative stress in astrocytes cultured from both young and old mice.

Example 2

The Protective Effect of ATP is Blocked by Pretreatment with Xestospongin C

The primary response of glial cells to extracellular ATP is an increase in intracellular $Ca^{2+}$. To investigate whether the protective effect of ATP could be initiated by a $Ca^{2+}$ response, we loaded cultures of astrocytes with the $Ca^{2+}$ indicator dye Fura-2 AM (10 $\mu$M for 30 minutes). Fura-2 fluorescence was imaged with 2-photon microscopy using 800 nm excitation. At this wavelength, fluorescence is primarily due to the $Ca^{2+}$ free form of fura-2. Hence, we expressed increases in $Ca^{2+}$ as decreases in fura-2 fluorescence ($\Delta F$) normalized by the resting fura-2 fluorescence ($F_{rest}$). When young astrocyte cultures were exposed to extracellular ATP (10 $\mu$M for 10 minutes), the peak intracellular $Ca^{2+}$ ($-\Delta F/F$) was increased to 0.46±0.02 (n=25, pooled from 2 experiments). A similar increase in the peak $Ca^{2+}$ amplitude was observed for astrocytes cultured from old mice ($-\Delta F/F$=0.46±0.04, n=11, pooled from 2 experiments). We tested whether the ATP-induced $Ca^{2+}$ response could be attributed to the metabotropic pathway, since $IP_3$ mediated $Ca^{2+}$ release can stimulate mitochondrial energy production as well as sensitize mitochondria to apoptotic stimuli. Astrocytes cultured from old mice were pretreated with Xestospongin C (XeC, 25 $\mu$M for 30 minutes), which is a competitive inhibitor of $IP_3$ binding to the $IP_3R$. When XeC-treated cultures were exposed to extracellular ATP (10 $\mu$M), the peak $Ca^{2+}$ response was significantly reduced to 0.28±0.04 (n=19 pooled from 2 experiments). These data suggested that at least part of the ATP-induced $Ca^{2+}$ response can be attributed to metabotropic P2Y receptor activation. This is consistent with other reports showing that activation of the ionotropic P2X receptor activation also increases $Ca^{2+}$ in cultured astrocytes. To determine whether the metabotropic pathway was involved with the protective effect of extracellular ATP, we subsequently exposed the XeC/ATP treated astrocytes to oxidative stress. As described above, the perfusate contained t-BuOOH (100 $\mu$M) and TMRE (200 nM) to monitor $\Delta\Psi$. Under these experimental conditions, the average time until $\Delta\Psi$ collapse was reduced to 5.48±0.22 (n=23, pooled from 2 experiments) in young astrocytes (FIG. 1C) and to 4.02±0.18 h (n=19, pooled from 2 experiments) in old astrocytes (FIG. 2C). These values were not significantly different from untreated astrocytes. We concluded that the protective effect of ATP on astrocytes was mediated by P2Y-receptors (P2Y-Rs).

Example 3

$IP_3$-BM Treatment Protects Astrocytes from Oxidative Stress

Figure 3A:
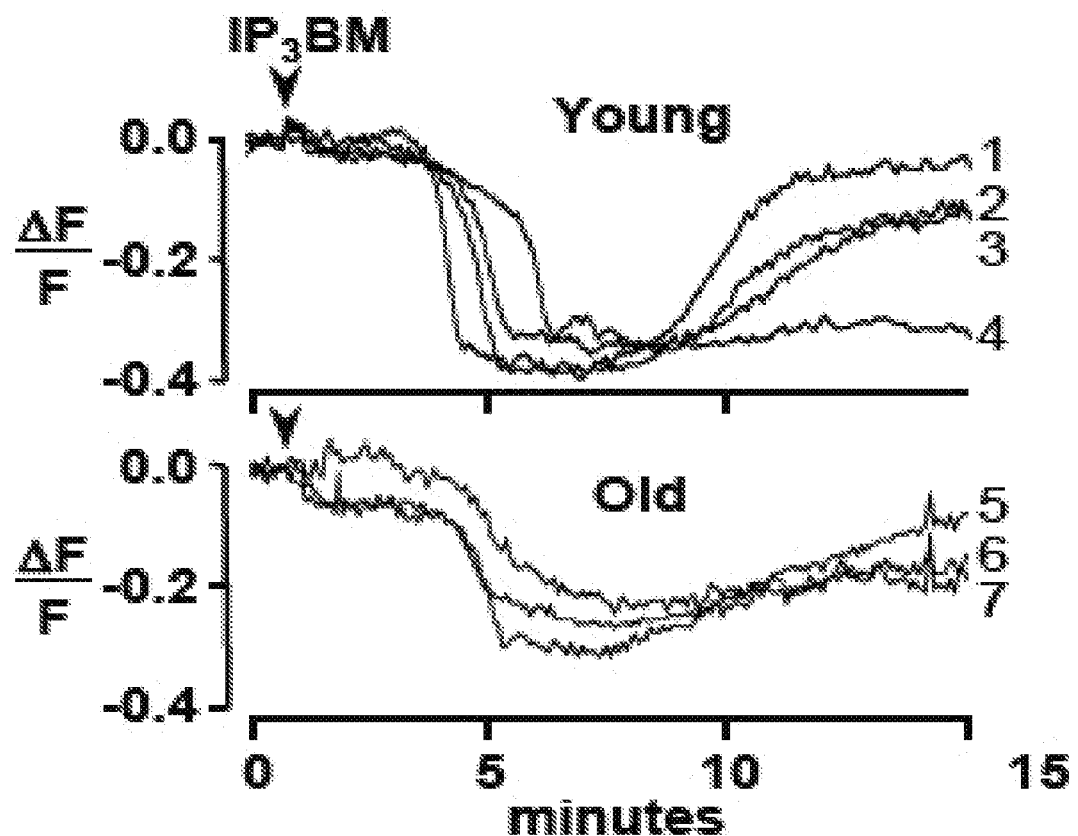
FIG. 3A depicts that $IP_3$-BM (25 µM, black arrowhead) increases intracellular $Ca^{2+}$ in both young and old astrocytes.
Figure 3B:
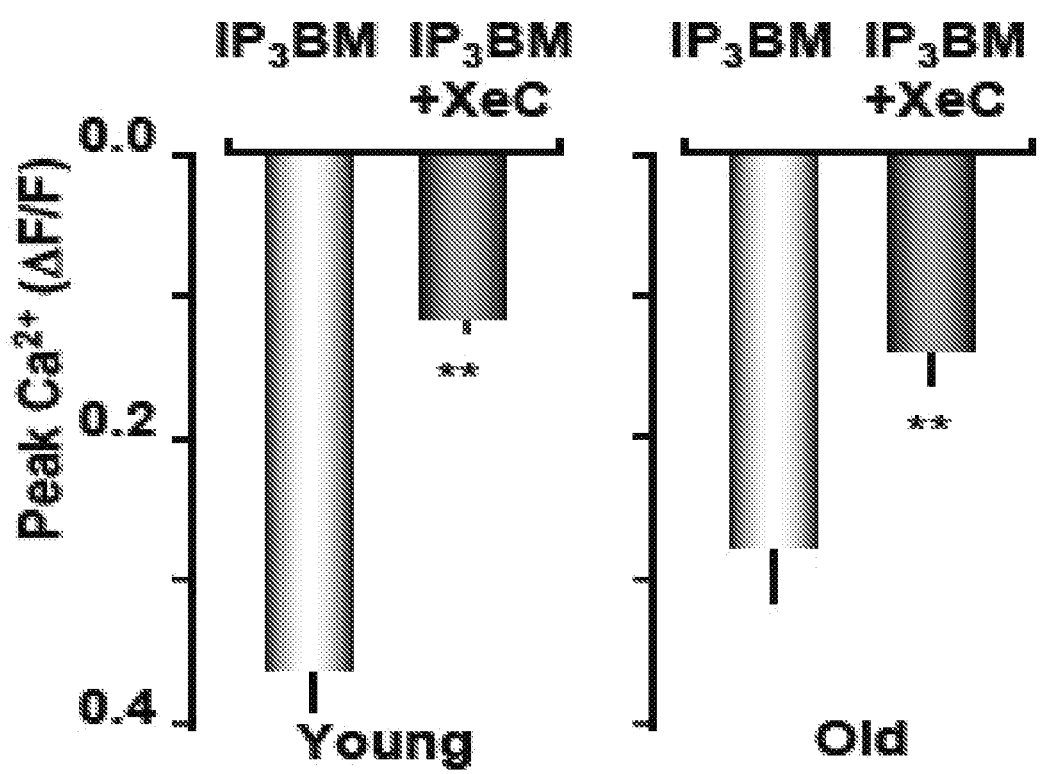
FIG. 3B depicts histogram plots of the peak $Ca^{2+}$ response for young and old astrocytes.
Figure 3C:
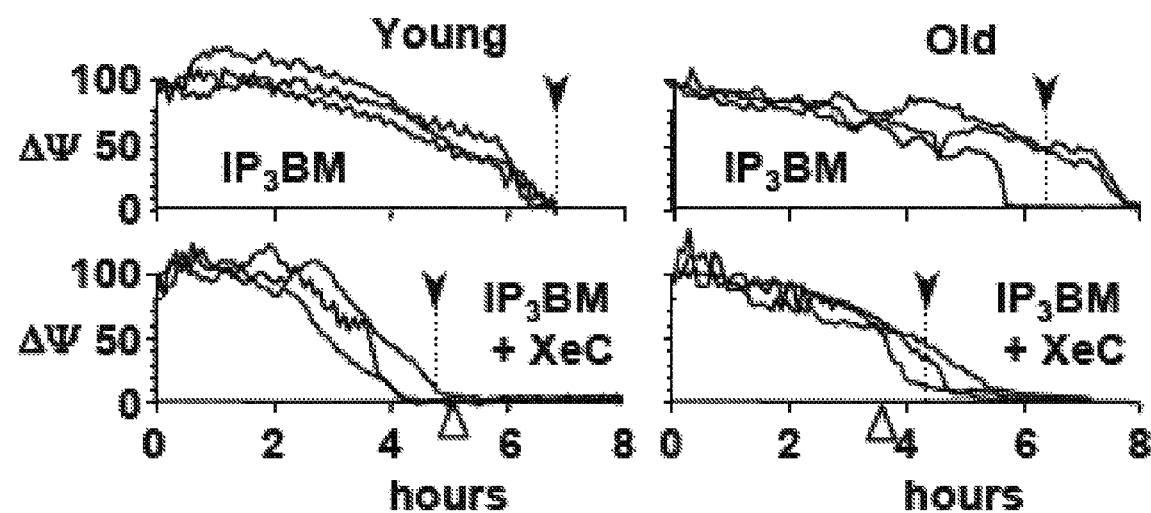
FIG. 3C Depicts intensity line plots of the mean TMRE fluorescence (ΔΨ) for 3 representative astrocytes pretreated with $IP_3$-BM (25 µM, 20 minutes) and subsequently exposed to oxidative stress (t-buOOH, 100 µM)
Figure 3D:
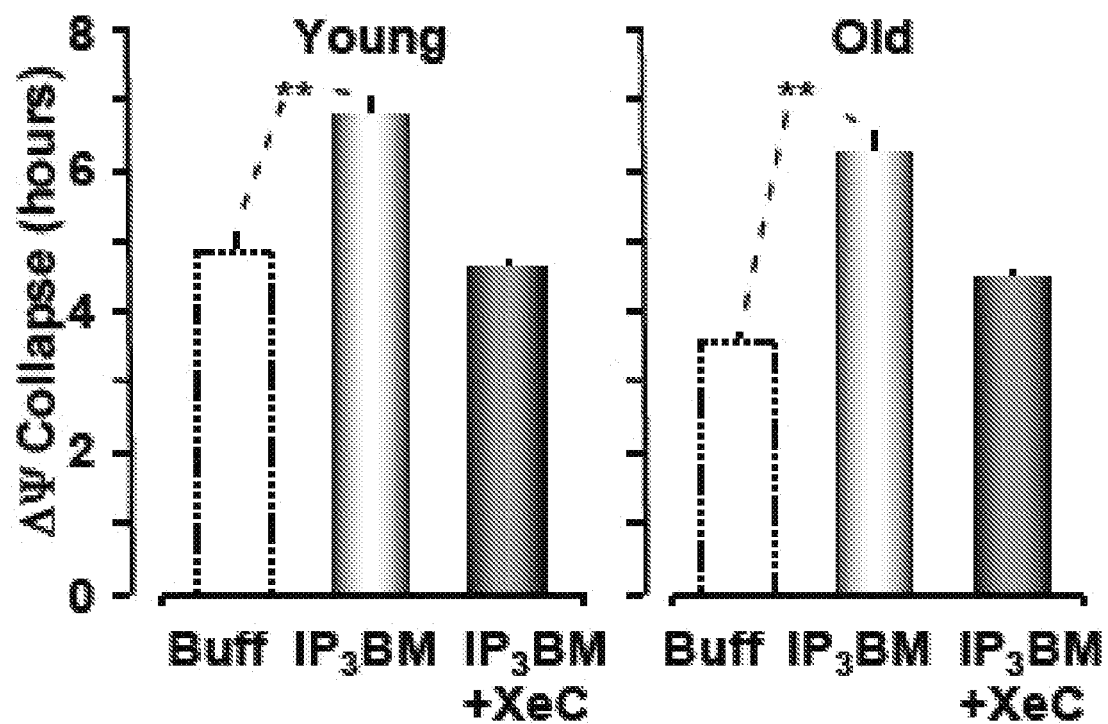
FIG. 3D depicts histogram plots of the mean times until ΔΨ collapse for astrocytes exposed to $IP_3$-BM or $IP_3$-BM plus XeC.

To directly investigate the role of metabotropic $IP_3/Ca^{2+}$ signaling pathway in the protective effect of P2Y-R activation, we examined the $Ca^{2+}$ response of astrocytes to butyryloxymethyl ester of $IP_3$ ($IP_3$-BM), a membrane permeant analog of $IP_3$. Cultured astrocytes were loaded with Fura-2 and imaged with 2-photon microscopy as described above. When cells were treated with $IP_3$-BM (25 $\mu$M), an increase in intracellular $Ca^{2+}$ was observed in astrocytes cultured from both young and old mice (FIGS. 3B, 3C). $Ca^{2+}$ increases for the indicated cell numbers are observed as decreases in signal intensity since the $Ca^{2+}$-free form of Fura 2 is preferentially excited at 800 nm. The peak $Ca^{2+}$ response was 0.34±0.02 (n=8, pooled from 2 experiments) for young astrocytes and 0.24±0.02 (n=24, pooled from 4 experiments) for old astrocytes. Overall, the $Ca^{2+}$ responses of astrocytes treated with IP$_3$-BM were slower than the comparable $Ca^{2+}$ responses for ATP treatment. This was expected because of the amount of time required to accumulate and activate IP$_3$-BM within cells. After fifteen minutes of IP$_3$-BM treatment, cultured cells were perfused with t-BuOOH and $\Delta\Psi$ was monitored with TMRE fluorescence. $\Delta\Psi$ traces from cells that were initially exposed to XeC (25 µM, 1 hour) prior to IP$_3$-BM treatment are presented in the bottom plots. The mean $\Delta\Psi$ collapse time for each plot is indicated by the vertical dotted lines and black arrowheads. The white arrow heads indicate the mean $\Delta\Psi$ collapse for buffer alone. We found that the time until $\Delta\Psi$ collapse was significantly increased to 6.82±0.32 (n=10, pooled from 1 experiment) in young astrocytes and to 6.32±0.35 (n=5, pooled from 1 experiment) in old astrocytes (FIGS. 3d,e). Again, the time until $\Delta\Psi$ collapse in IP$_3$-BM-treated old astrocytes was significantly longer than the time until $\Delta\Psi$ collapse in untreated cultures of young astrocytes. Pretreatment of young and old astrocytes with XeC (25 µM for 30 minutes) significantly reduced their $Ca^{2+}$ responses to 0.11±0.01 (n=13, pooled from 1 experiment) and 0.13±0.01 (n=18, pooled from 2 experiments) (FIG. 3B). Furthermore, XeC completed inhibited the protective effect of IP$_3$-BM on young and old astrocytes. The time until $\Delta\Psi$ collapse was reduced to 4.73±0.05 (n=16, pooled from 2 experiments) in young astrocytes and to 4.48±0.07 (n=18, pooled from 2 experiments) in old astrocytes (FIG. 3D). Dotted line histogram bars are presented as control (Buff only) references. Neither of these values were significantly different than those observed in untreated cells. We concluded from these data that IP$_3$-mediated intracellular $Ca^{2+}$ release protects astrocytes from oxidative stress.

Example 4

Figure 4A:
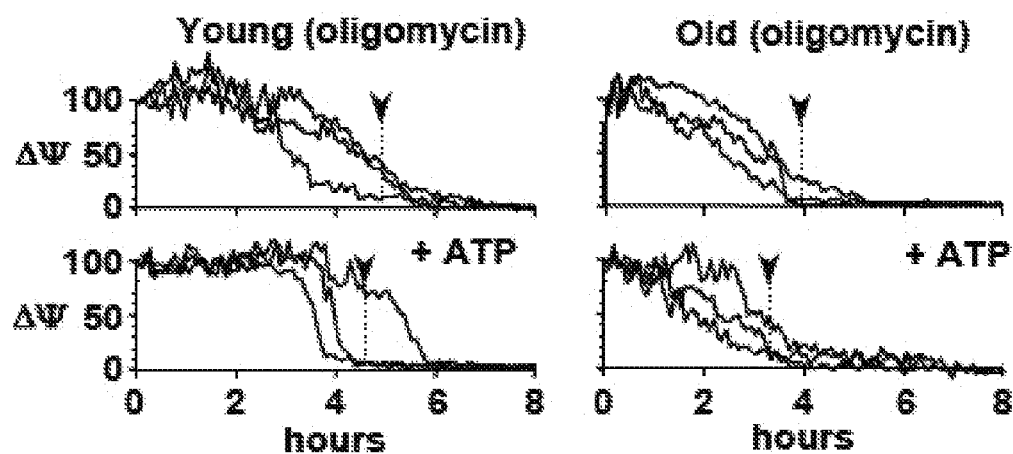
FIG. 4A depicts intensity line plots of the mean TMRE fluorescence (ΔΨ) for representative astrocytes pretreated with oligomycin (10 µg/ml, 1 hour) and subsequently exposed to oxidative stress (t-buOOH, 100 µM) with (top traces) and without P2Y-R stimulation (10 µM ATP, 10 minutes)
Figure 4B:
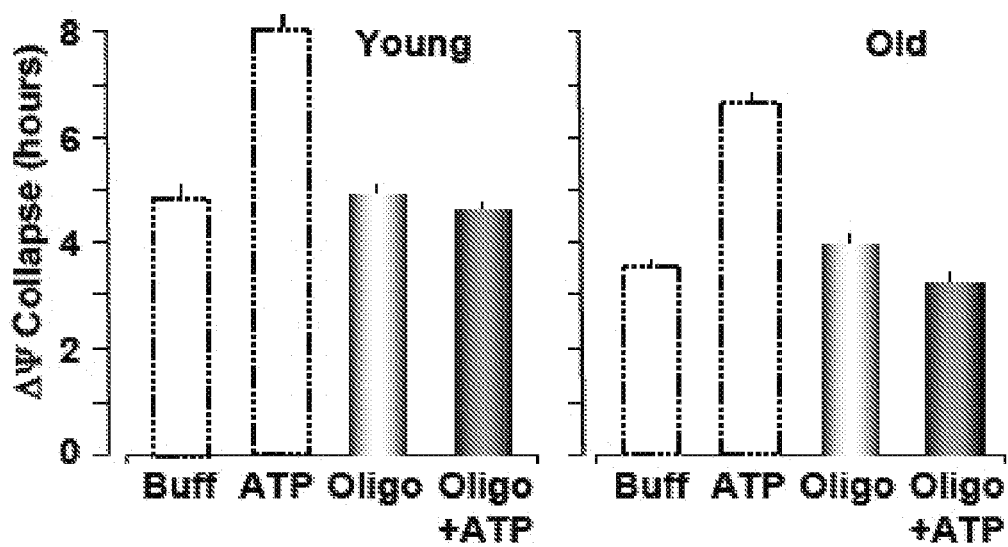
FIG. 4B depicts histograms of the mean ΔΨ collapse times during oxidative stress (t-buOOH, 100 µM)

Oligomycin Blocks the Protective Effect of P2Y-R Activation Against Oxidative Stress A potential mechanism by which IP$_3$-mediated intracellular $Ca^{2+}$ release could provide protection to a cell is by increasing intracellular production of ATP via a $Ca^{2+}$-mediated increase in mitochondrial respiration. To initially test this mechanism of action, we pretreated cultured astrocytes with oligomycin (1 µg/ml for 30 minutes), a specific inhibitor of the mitochondrial ATP synthetase. We found that the time until $\Delta\Psi$ collapse was 5.15±0.08 (n=21, pooled from 2 experiments) in young astrocytes and 4.16±0.14 h (n=23, pooled from 2 experiments) in old astrocytes exposed oxidative stress (t-buOOH, 100 µM) (FIG. 4A). Vertical dotted lines with black arrowheads indicate the mean $\Delta\Psi$ collapse times. These times until $\Delta\Psi$ collapse were comparable to control values of untreated astrocytes, suggesting the acute pretreatment of astrocytes with oligomycin did not affect their resistance to oxidative stress. However, when oligomycin-treated astrocytes were exposed to extracellular ATP for 10 minutes, we found that P2Y-R activation no longer enhanced their resistance to oxidative stress. The mean time until $\Delta\Psi$ collapse was 4.69±0.23 (n=34, pooled from 3 experiments) in young astrocytes and 3.21±0.08 (n=6, pooled from 1 experiment) in old astrocytes. FIG. 4B depicts histograms of the mean $\Delta\Psi$ collapse times during oxidative stress (t-buOOH, 100 µM). These values were indistinguishable from the mean $\Delta\Psi$ collapse times observed in untreated astrocytes. Taken together, these data suggested that astrocyte mitochondrial ATP production was required for the protective effect of P2Y-R activation against oxidative stress.

Example 5

Figure 5A:
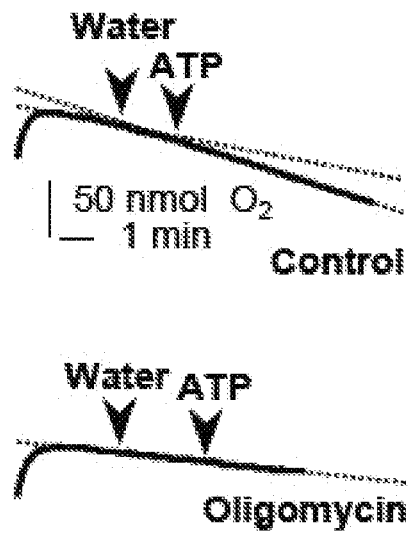
FIG. 5A depicts plots of $O_2$ levels in suspended astrocytes as labeled.
Figure 5B:
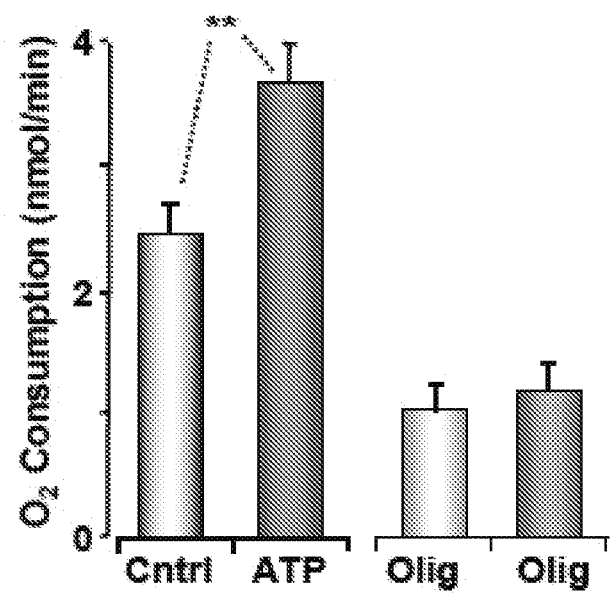
FIG. 5B depicts a histogram showing the average change in $O_2$ consumption with 2 µM ATP compared to untreated cells (control). Bars on the right show $O_2$ consumption of Astrocytes are preloaded 0.01 uM Oligomycin (30 minutes)

P2Y-R Activation in Astrocytes Stimulates $O_2$ Consumption and Intracellular ATP Production To further investigate the importance of mitochondrial metabolism on the protective effect of P2Y-R activation, we first measured the rate of $O_2$ consumption for astrocytes with and without P2Y-R activation. Primary cultures of astrocytes were grown to ~70% confluency, gently removed by trypsin EDTA and resuspended in PBS buffer. Astrocytes ($10^5$ cells/ml) were then loaded into a 500 µl Respirometer Chamber MT200A) and maintained at 37° C. by a circulating water bath. FIG. 5A depicts plots of $O_2$ levels in suspended astrocytes as labeled. FIG. 5B depicts a histogram showing the average change in $O_2$ consumption with 2 µM ATP compared to untreated cells (control). Bars on the right show $O_2$ consumption of Astrocytes are preloaded 0.01 uM Oligomycin (30 minutes). We found that the basal rate of $O_2$ consumption in astrocytes was 2.45±0.24 nmol/min (n=3). This rate increased significantly (p<0.01) to 3.67±0.3 nmol/min (n=3) when astrocytes were stimulated by a bolus of ATP (2 µM final concentration). The rate of $O_2$ consumption was significantly decreased (p value<0.01) to 0.97±0.21 nmol/min (n=4) after exposing the astrocytes to the ATP synthetase inhibitor oligomycin (0.01 µM, 30 minutes). Oligomycin treatment also completely inhibited the effects of extracellular ATP on the rate of $O_2$ consumption (1.19±0.27 nmol/min, n=3).

Figure 5C:
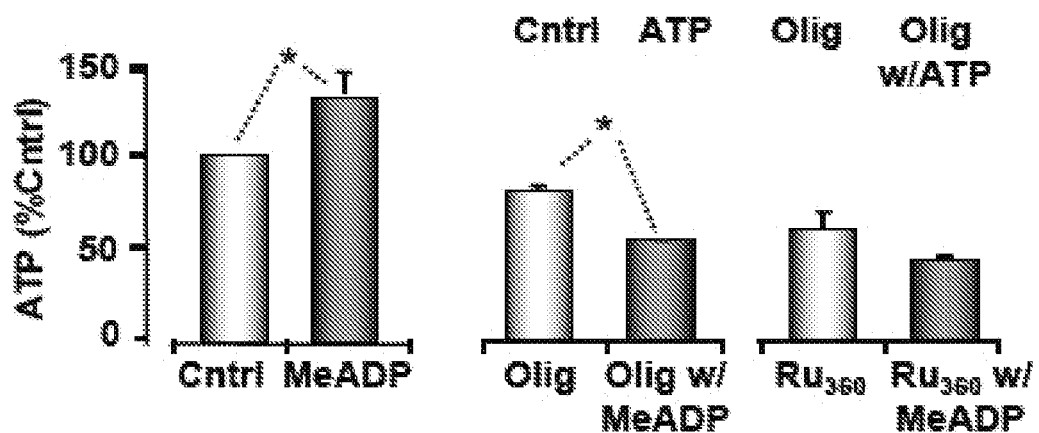
FIG. 5C depict histograms of the direct measurement of intracellular ATP levels relative to untreated cells (control), P2Y-R stimulated (MeADP), then the same measurements in the presence of oligomycin (oligo) or ruthenium 360 ($Ru_{360}$)
Figure 5D:
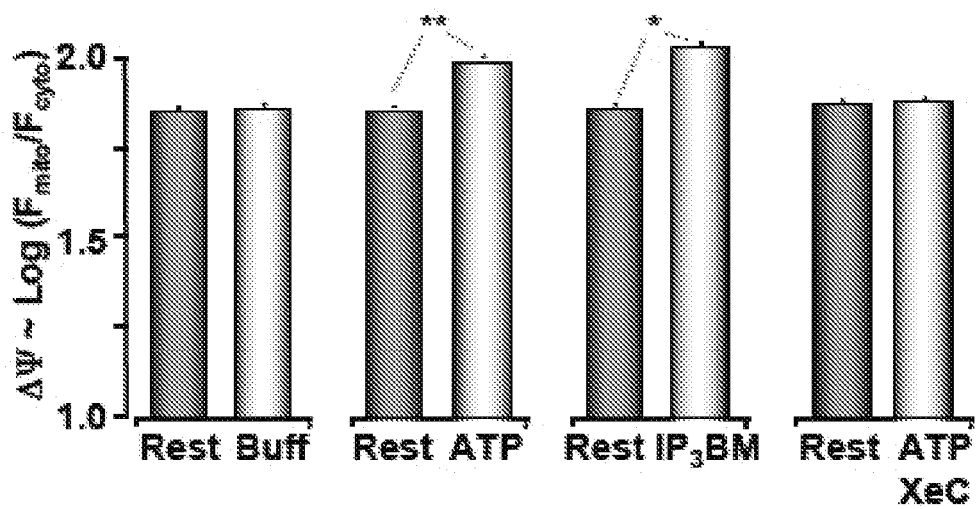
FIG. 5D depicts histogram plots showing average mitochondrial membrane potentials before and after treatment.

Our next approach to investigate the role of mitochondrial metabolism was to directly measure ATP levels in cultures astrocytes using a luciferin-luciferase assay (Invitrogen). Astrocytes were cultured as described above, trypsinized and washed with buffer. The cells were then suspended in a lysate buffer and immediately heated to 100° C. (5 min) to minimize enzymatic changes in ATP levels. After centrifugation, the ATP dependent luminescence of supernatant was measured with a microplate reader (Biotek). FIG. 5C depicts histograms of the direct measurement of intracellular ATP levels relative to untreated cells (control), P2Y-R stimulated (MeADP), then the same measurements in the presence of oligomycin (oligo) or ruthenium 360 (Ru$_{360}$). We estimated that the resting intracellular ATP concentration in cultured astrocytes was 0.31±0.14 µM ATP/$10^4$ cells (n=3). Treatment of cultured astrocytes with the P2Y$_1$-R specific ligand 2-Me-SADP (2 µM) for 10 minutes significantly increased ATP levels to 0.39±0.16 µM ATP/$10^4$ cells (p<0.04). These data are also presented as a percentage of the control values for each experiment (n=3, FIG. 5C), which were used to test statistical significance with paired Student t-Tests. Oligomycin (0.01 µM, 30 min) significantly decreased the resting levels of ATP to 82.6%±3.2% of control (p<0.05, n=3). The same oligomycin pretreatment also completely inhibited P2Y$_1$-R mediated increases in ATP. Finally, we tested whether ruthenium 360 (Ru$_{360}$; Calbiochem), a polycation that inhibits the electrogenic mitochondrial $Ca^{2+}$ uniporter, affected mitochondrial ATP production. We found that Ru$_{360}$ treatment (1 µM, 30 min) significantly decreased the basal ATP levels to 60.5%±10.5% (n=3) of control values and also completely blocked the ability of P2Y$_1$-R specific ligand, 2-MeSADP to increase ATP levels. Taken together, these data strongly suggest that P2Y-R stimulation leads to an IP$_3$-mediated intracellular $Ca^{2+}$ release that increases intracellular production of ATP via a $Ca^{2+}$-mediated increase in mitochondrial respiration.

Example 6

Extracellular ATP and IP$_3$-BM Treatment Increase ΔΨ

Our observation that P2Y-R enhanced protection of astrocytes was mediated by an increase in the intracellular production of ATP indicated that mitochondrial membrane potential (ΔΨ) was also increased. We confirmed this by directly measuring the effect of ATP, ATP plus XeC and IP$_3$-BM treatments on ΔΨ. Cultured cells were labeled with TMRE (200 nM) and imaged with a two-photon microscope as described above. ΔΨ was estimated as the log ($F_{mito}/F_{cyto}$) where $F_{mito}$ is the peak fluorescent intensity observed in single mitochondria (Farkas et al., 1989; Lin et al., 2005). The mean values of individual mitochondria from a single cell were used for the mitochondrial potential estimate. $F_{cyto}$ represents the lowest value of TMRE fluorescence observed within the boundaries of the same cell. Prior to each treatment, the resting ΔΨ was comparable between experiments. FIG. 5E depicts a histogram plot showing average mitochondrial membrane potentials before and after treatment. The mean resting ΔΨs for untreated (Buffer), ATP-treated, ATP plus XeC-treated and IP$_3$-BM-treated were 1.84±0.01 (n=78 mitochondria, pooled from 2 experiments), 1.84±0.01 (n=85 mitochondria), 1.85+0.01 (n=80 mitochondria) and 1.86+0.01 (n=48 mitochondria), respectively. Astrocyte cultures were then exposed to their respective treatments and the same fields of mitochondria were imaged 10 minutes later. As expected, the control untreated cells exhibited no change. ΔΨ remained at 1.85±0.01 (n=83 mitochondria). However, treating astrocytes for 10 minutes with ATP or IP$_3$BM significantly increased ΔΨ to 1.98±0.01 (n=89 mitochondria) and 2.02±0.01 (n=77 mitochondria), respectively. Furthermore, astrocytes pretreated with XeC and then exposed to ATP exhibited no significant change in ΔΨ, which was 1.87±0.01 (n=50 mitochondria). These data are consistent with the model that P2Y-R activation in astrocytes stimulates IP$_3$ mediated intracellular $Ca^{2+}$ release, which increases mitochondrial matrix $Ca^{2+}$, stimulating respiration and the subsequent production of intracellular ATP.

Example 7

P2Y-R Activation in Astrocytes Increases Neuroprotection

Figure 6A:
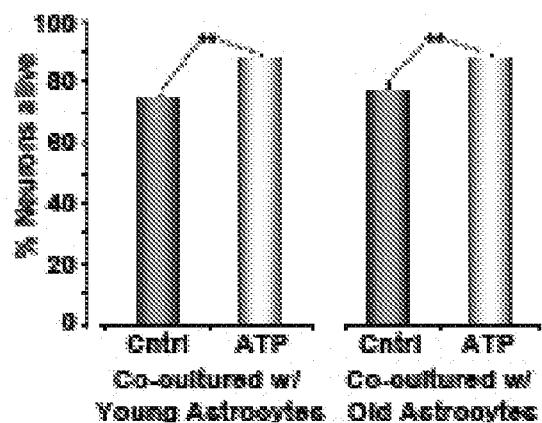
FIG. 6A depicts histogram plots of the percentage of neurons alive when cocultured with young or old astrocytes.
Figure 6B:
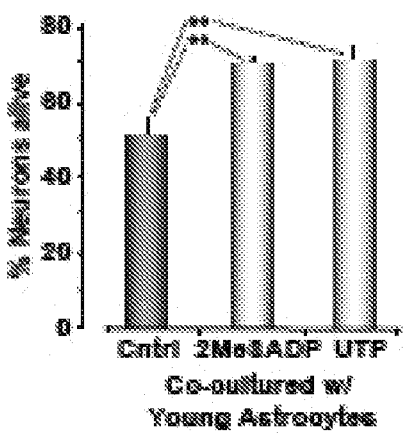
FIG. 6B depicts histogram plots of the percentage of neurons alive pretreated with either 2-MeSADP (2 µM) or UTP (50 µM) for 10 min.

To determine whether P2Y-R enhanced mitochondrial metabolism in astrocytes affected neuronal resistance to oxidative stress, we prepared co-cultures of neurons and astrocytes using corning transwell-clear permeable supports, which physically separates the two cell-types by ~1 mm (# 07-200-170, Fisher scientific). Primary cultures of astrocytes were directly prepared in transwell supports until they were ~70% confluent. Mouse cortical neurons were then cultured onto glass bottom mattek plates and maintained in B-27/Neurobasal Medium to control glia contamination to less than 0.5% (Invitrogen). After four days, co-cultures were treated with t-buOOH (100 μM) for 4 hours with and without pre-stimulation of ATP (2 μM, 10 minutes). Cells were then stained with the DNA intercalating dye Hoechst 33342 (10 μg/ml, Molecular Probes, #H-3570) and calcein AM (2 μM, Molecular Probes, #C3100). Cell viability was quantified by counting the number of nuclei that did not co-localize with calcien stained cells, which is only observed in live cells that have maintained their plasma membrane integrity. We found that purinergic receptor activation significantly enhanced neuronal survival from 74±2% (n=1332 cells, pooled from 4 experiments) to 87±2% (n=1914 cells, pooled from 5 experiments) when co-cultured with young astrocytes and from 77±3% (n=1092 cells, pooled from 4 experiments) to 87±2% (n=2510 cells, pooled from 6 experiments) when co-cultured with old astrocytes. We then tested the neuroprotective affects of isoform specific purinergic ligands 2-MeSADP(P2Y$_1$-R) and UTP(P2Y$_2$-R). FIG. 6A depicts histogram plots of the percentage of neurons alive when cocultured with young or old astrocytes. FIG. 6B depicts histogram plots of the percentage of neurons alive pretreated with either 2-MeSADP (2 μM) or UTP (50 μM) for 10 min. A ten-minute pre-treatment of astrocytes with either 2-MeSADP (2 μM), or UTP (50 μM) was equally protective against oxidative stress induced cell death. The % neurons alive after 4.5 hours of t-buOOH treatment was 51±4% (n=1664 neurons, pooled from 4 experiments) for untreated controls, 70±2% (n=2541 neurons, pooled from 4 experiments) for 2-MeSADP and 71±3% (n=1189 neurons, pooled from 4 experiments) for UTP treated co-cultures. P2Y-R specific ligands also increased the resistance of primary cultures of astrocytes, in the absence of neurons. The % astrocytes alive after 4.5 hours of t-buOOH treatment, in the absence of neurons, was 60±4% (n=294 cells) for control, 77±4% (n=294) for 2-MeSADP and 79±3% (n=333) for UTP treated astrocytes.

Figure 6C:
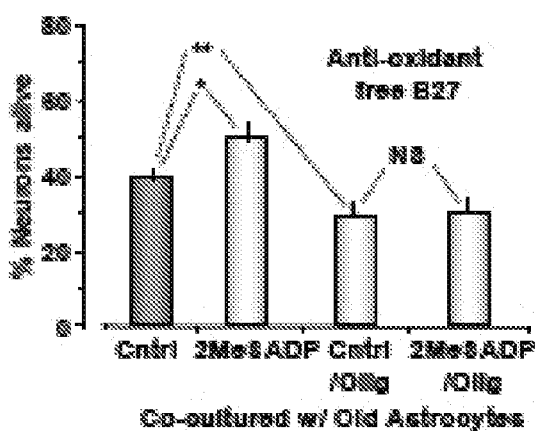
FIG. 6C depicts histogram plots of the percentage of neurons alive that were precultured with astrocytes but were separated before pretreating (10 min) the neurons with either ATP (2 µM ATP; 10 min) or 2-MeSADP (2 µM) and subsequently exposed to oxidative stress (100 µM; t-BuOOH; 4.5 h)
Figure 6D:
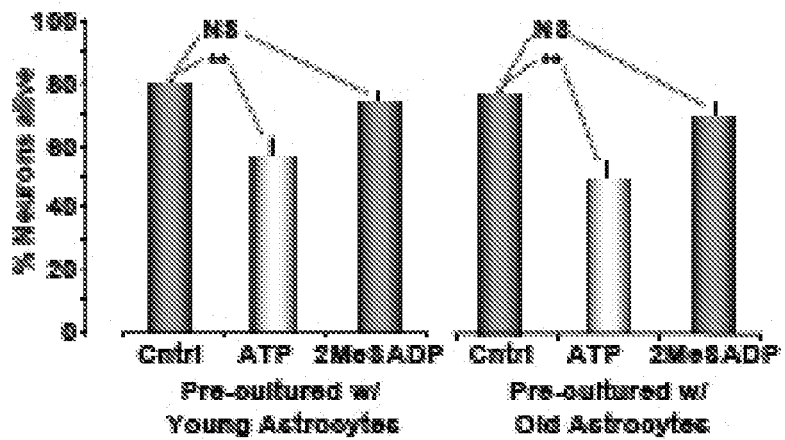
FIG. 6D depicts histogram plots of percentage of neurons alive cocultured with old astrocytes using anti-oxidant free B-27 supplement for 3 h.
Figure 6E:
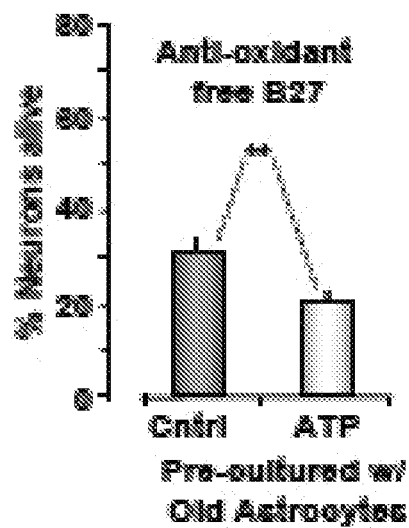
FIG. 6E depicts the same experiment as in FIG. 6D except using anti-oxidant free B-27 supplement.

Since it is known that B-27 supplement has antioxidant properties, we also repeated the above experiments using an anti-oxidant-free B-27, also available form Invitrogen, to control glia contamination. FIG. 6C depicts histogram plots of the percentage of neurons alive that were precultured with astrocytes but were separated before pretreating (10 min) the neurons with either ATP (2 μM ATP; 10 min) or 2-MeSADP (2 μM) and subsequently exposed to oxidative stress (100 μM; t-BuOOH; 4.5 h). FIG. 6D depicts histogram plots of percentage of neurons alive cocultured with old astrocytes using anti-oxidant free B-27 supplement for 3 h. FIG. 6E depicts the same experiment as in FIG. 6C except using anti-oxidant free B-27 supplement. Procedures were identical to those described above except that after four days of co-culturing, dishes were treated with t-buOOH (100 μM) for only 3 hours with and without pre-stimulation of 2-MeSADP (2 μM, 10 minutes). Cells were then stained with Hoechst 33342 and calcein AM to ascertain cell viability. We found that the % neurons alive after 3 hours of treatment was reduced to 33±2% (n=1322 cells, pooled from 4 experiments). However, a 10 minute treatment of co-cultures with 2-MeSADP (2 μM) significantly enhanced neuronal survival to 43±3% (n=1057 cells, pooled from 3 experiments, p<0.03). In addition, oligomycin treatment significantly (0.01 μM, 30 minutes, p<0.01) decreased neuronal survival to 25±3% (n=1409 cells, pooled from 3 experiments), and completely inhibited the protective effects of 2-MeSADP on neuronal survival (26±3%, n=1048 cells, pooled from 3 experiments).

It should be noted that stimulation of neuroprotective response in astrocytes is not restricted to signaling through P2Y receptors. For example we have shown that administration of the membrane permeable IP$_3$ analog, IP$_3$BM, is capable of protecting astrocytes from oxidative damage. Thus, it appears possible that any stimulus capable of evoking IP$_3$-mediated calcium release in astrocytes is equally suitable for application in the present treatment methods. To test this possibility, astrocyte cultures subjected to oxidative stress were treated with either 2-MeSADP, or the metabotropic glutamate receptor agonist (1 S, 3 R)-1-aminocyclopentane-1,3-dicarboxylic acid (ACPD), or were left untreated. The histogram depicted in FIG. 6B clearly demonstrates that astrocyte resistance to oxidative stress is enhanced by treatment with either a P2Y-R agonists or an mGluR agonist. This, in combination with the results shown earlier, strongly suggests that astrocytes neuroprotection and resistance to oxidative insult are enhanced by stimuli that evoke $IP_3$-mediated $Ca^{2+}$ release in astrocytes.

Activation of neuronal P2X receptors has been reported neurotoxic. Consequently, we further examined the affects of P2Y-R activation on neuronal survival in the absence of astrocytes. Neurons were co-cultured with astrocytes in transwell dishes that were removed from the cultures just prior to treating the neurons with purinergic ligands. Neurons in the absence of astrocytes were then exposed to t-buOOH (100 μM, 4.5 hours with normal B-27, 3 hours with antioxidant-free B-27) and cell viability was assessed by the ability of neurons to retain calcien. Under these conditions, we discovered that purinergic receptor activation by ATP treatment decreased cell viability, consistent with published reports. With normal B-27 supplement, the % neurons alive was significantly decreased to 56±7% (n=1192 cells, pooled from 4 experiments, p<0.005) by ATP treatment while control, untreated neurons were at 80±2% (n=1049 cells, pooled from 4 experiments). When the neurons were pretreated with 2-MeSADP, the % neurons alive (74±3%, n=892 cells, pooled from 4 experiments) was not significantly different from control. The same results were found for neurons initially co-cultured with old astrocytes. The % neurons alive was 77±2% (n=1057 cells, pooled from 4 experiments) for untreated controls, 49±6% (n=1197 cells, pooled from 4 experiments p<0.001) for ATP treated neurons, and 72±3% (n=1182 cells, pooled from 4 experiments) for 2-MeSADP treated neurons. We obtained similar results when using the anti-oxidant-free B-27 as a supplement. The % neurons alive was significantly decreased to 18±2% (n=763 cells, pooled from 3 experiments, p<0.01) by ATP treatment while control, untreated neurons were at 27±3% (n=840 cells, pooled from 3 experiments). We conclude from these data that the neurotoxic affect of purinergic stimulation is likely mediated by P2X receptors, as reported by others, while P2Y-R stimulation in neurons has no significant toxicity.

Example 8

Rose-Bengal Induced Blood Clot Transiently Increases $Ca^{2+}$ in Nearby Astrocytes Our working hypothesis states that P2Y-R activation in astrocytes leads to intracellular $Ca^{2+}$ release. In preliminary studies, we have obtained evidence consistent with the model suggesting that stimulation of P2Y-Rs increases intracellular $Ca^{2+}$ release. In this experiment, the $Ca^{2+}$ indicator Fluo4-AM was loaded into astrocytes (90 minutes, 100 μM). Rose Bengal (RB) and the P2Y-R specific agonist 2-MeSADP were then co-injected in the tail vein of a live mouse. RB was illuminated with green light (543 nm), inducing reactive singlet oxygen and blood clots. A blood vessel was free flowing at 180 minutes, then clotted around 220 minutes after RB injection. Clot formation resulted in a breakdown of the blood brain barrier in this region, permitting 2-MeSADP to leak into the brain and activate nearby astrocytes. More distal astrocytes a4 and a5 were not activated.

Example 9

Activation of P2Y-R Protects Astrocytes from Ischemia-Induced Oxidative Stress

Figure 7:
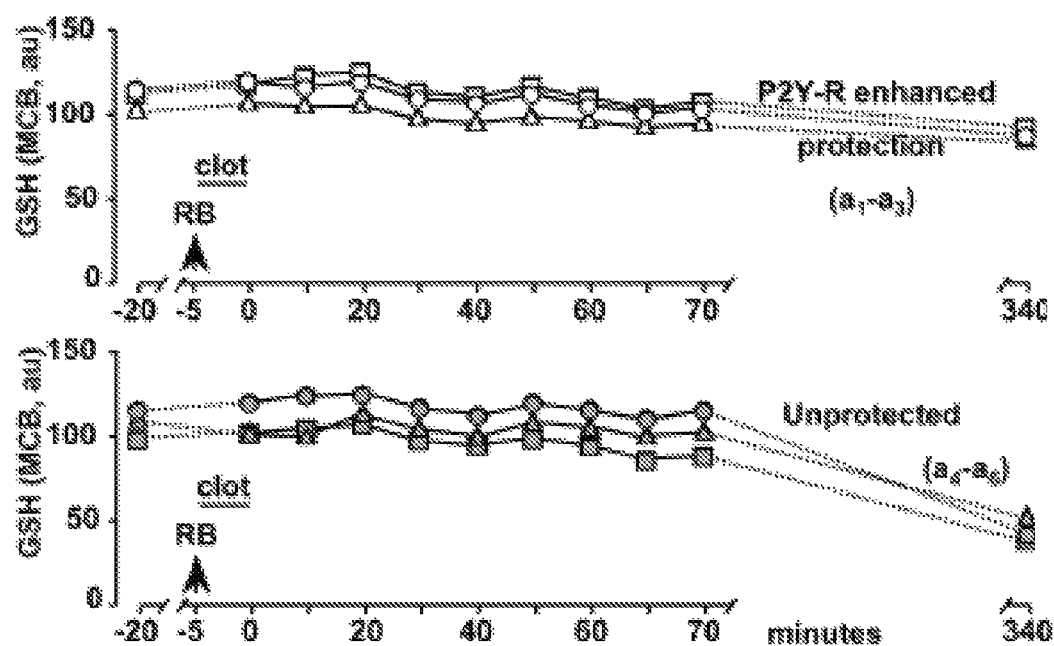
FIG. 7 depicts lineplots of MCB fluorescence of astrocytes protected (a1-a3) and not protected (a4-a6) by p2Y-R.

In another series of experiments, a transgenic mouse expressing green fluorescent protein (GFP) in astrocytes was prepared for imaging. In this mouse, the cortical cells were labeled with monochlorobimane (MCB), a fluorescent indicator of reduced GSH. After obtaining an image of astrocytes (GFP) and MCB fluorescence, the mouse was tail vein injected with Rose Bengal (RB), FITC-dextran and the P2Y-R agonist 2-MeSADP. A clot was induced with 543 nm irradiation in a region of the brain. Breakdown of the blood brain barrier in the region near this clot permitted secretion of 2-MeSADP in the nearby astrocytes. MCB fluorescence was maintained for over an hour in all of the cells in the field of view. However, when the same field was viewed again at 340 minutes, the entire field was now ischemic, but the astrocytes near the clot still exhibited strong GSH levels. The persistence of GSH in this area indicates an enhanced region of protection against oxidative stress caused by ischemia. Line-plots of MCB fluorescence of the astrocytes is depicted in FIG. 7. Cells a1-a3 are within the protected zone and cells a4-a6 are outside this area. Note that MCB fluorescence is reduced to under 50% 340 minutes (5 hours 40 minutes) after the initial clot for unprotected astrocytes (a4-a6) while the MCB fluorescence is essentially maintained near the initial clot zone that was exposed to P2Y-R agonist.

Example 10

Systemic Administration of the P2Y1-R Agonist 2-MeSADP Decreases the Size of Rb-Induced Cerebral Infarcts in the Mouse Cortex These set of experiments utilizes small animal imaging studies to non-invasively study the impact of G-protein stimulated IP3-gated $Ca^{2+}$ release on astrocyte neuroprotection during the aging process. In brief, focal cerebral infarcts are induced using photothrombosis as described in EXAMPLE 8. However, irradiation of the brain with green light is carried out through the cranium with a 10× objective. This results in ~1-2 mm lesion. We observe the size of the lesion in subsequent days by taking advantage of an inflammatory response at the lesion, which we label with a fluorescently conjugated antibody to CD40 (PE-Cy5.5-anti-mouse-CD40). It has been demonstrated that CD40 ligand contributes to the inflammatory and prothrombogenic responses of a brain infarction. It has also been reported that the PE-Cy5.5 CD40 antibody localized to activated endothelium at the brain lesion and to blood derived cells of the mononuclear lineage. We have successfully used this approach to image RB-induced brain inflammation in mice with high sensitivity and specificity. These data indicate that P2Y1-R activation at the whole animal level appears to be neuroprotective. To carry out these experiments, 3 mice were imaged. On the day of the initial photothrombosis, one mouse was injected with Rose Bengal, one with Rose Bengal and 2-MeSADP and the third mouse was injected only with saline. On day 3 after the initial cerebral infarction, the size of the lesion was significantly smaller in mice co-injected with Rose Bengal the P2Y1-R agonist in comparison with Rose Bengal or saline alone. For one set of mice, we re-imaged the mice at day 17 post occlusion and found CD40 labeling undetectable in the 2-MeSADP injected mouse. This experiment demonstrates that we can follow the progression of cerebral infarcts for over 2 weeks using this approach. Finally, in one mouse, we also injected a fluorescent dye (IR-820) on day 3 that is a strong indicator of blood brain barrier dysfunction. Accumulation of this dye at the site of a lesion is consistent with a permeant (i.e., compromised) blood brain barrier.

Example 11

As noted above small animal imaging has been successfully employed to progressively follow and measure the size of Rose Bengal (RB)-induced brain infarcts in live mice for over 2 weeks. Our data show that the size of the cerebral infarct is reduced when the P2Y1-R ligand 2-MeSADP is present during the initial photothrombosis (day 0) as well as when the P2Y1-R ligand is introduced 24 hours later. Our previous work in cell culture demonstrated that inhibition of the mitochondrial ATP synthetase with oligomycin completely blocked P2Y-R enhanced neuroprotection.

A critical role for mitochondrial metabolism is also supported by new data obtained from a transgenic mouse model expressing a mitochondrial targeted DNA restriction enzyme, EcoR1, under the control of doxycycline (tTA/mtEcoR1, courtesy of Dr. Chris Walters, UTHSCSA). Expression of mtEcoR1 severely limits mitochondrial metabolism and astrocytes cultured from these transgenic mice did not exhibit increased resistance to oxidative stress when P2Y-Rs were activated (unpublished data). In addition, P2Y1-R activation did not protect tTA/mtEcoR1 mice from RB-induced cerebral infarcts. In addition to optically imaging multiple physiological parameters in single cells (e.g. mitochondrial membrane potentials and Ca2+ levels in real time), we have successfully imaged single cells edema formation in response to a Rose Bengal (RB)-induced photothrombotic event in a single blood vessel. Our preliminary measurements indicate that astrocyte volume increases over 6-fold during edema formation. Moreover, tail-vein injection of the P2Y1-R ligand, 2-MeSADP, significantly reduced swelling and appeared to completely reverse astrocyte swelling within 8 hours of the initial clot.

Example 12

A precise clot in a blood vessel is induced using the photosensitive dye Rose Bengal (RB) in the mouse cortex. The blood vessels were simultaneously imaged by injecting the red fluorescent dye Rose Bengal (RB) into the mouse circulation. The targeted blood vessel is illuminated by a 543-nm laser after tail vein injection of RB. RB is activated by the laser and interacts with molecular oxygen to form singlet oxygen, which is known to damage endothelial cells within the blood vessel, thereby triggering the natural clotting cascade and leading to formation of a clot. Pharmacological agents can be introduced at the time of photoactivation which also causes the breakdown of the blood-brain barrier.

The parietal cortex of GFAP-GFP transgenic mice was imaged using confocal microscopy and a 40×NA 0.8 or 10×NA 0.45 objective. The same region of the cortex was periodically imaged prior to RB injection, and 10, 20, 30, and 40 minutes post-RB injection. RB is impermeable to the BBB and is cleared quickly under physiological conditions. Increased BBB permeability was seen following photothrombosis, exhibited by increased RB fluorescence outside of the clotted vessel. Reperfusion of the mouse with RB 48 hours after photothrombosis showed that the BBB remains disrupted for at least 2 days.

Figure 8:
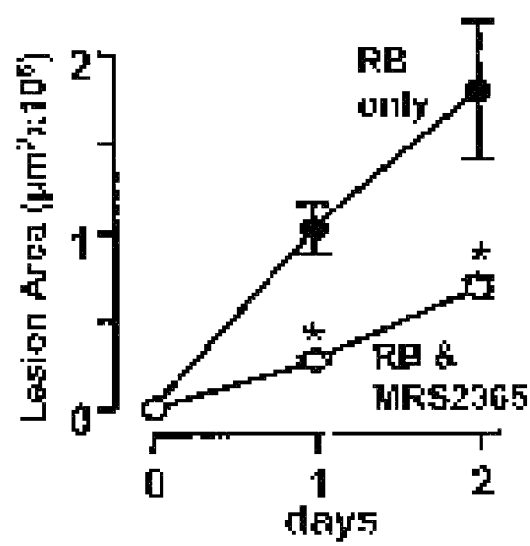
FIG. 8 depicts P2Y1-R enhanced protection of Rose Bengal (RB)-induced cerebral infarcts in mouse cortex by MRS2365.

The parietal cortex of GFAP-GFP transgenic mice was imaged using confocal microscopy and a 10×0.45 NA objective. A z-stack of 120 images (2 µm step) was acquired before and after RB-induced photothrombosis, with and without the $P2Y_1R$ agonist, MRS2365. The same region of the cortex was periodically imaged prior to ischemia as well as 24 and 48 hours post-ischemia. Each image was produced by compiling overlapping individual images based on maximum intensity pixel projection using image J to create a mosaic image. The size of the lesion was calculated in Image J by tracing the region of the cortex that was void of GFP expressing astrocytes. A plot of the average lesion sizes with respect to time is depicted in FIG. 8. Statistical analysis clearly demonstrates that inclusion of the $P2Y_1R$ agonist, MRS2365, greatly reduces the size of the lesion.

Discussion Of Experimental Results

Accumulation of oxidative damage as the result of normal mitochondrial metabolism is widely considered to be a fundamental cause of aging. A central tenet of this theory is that mitochondria themselves become dysfunctional. In the CNS, the focus of aging research has primarily revolved around changes in and effects of neuronal mitochondrial metabolism. However, there is increasing interest in the role that astrocyte mitochondria play in the aging process. Little is known about the cumulative effects of aging on astrocyte mitochondria or on energy dependent processes within astrocytes. It is likely that diminished astrocyte function throughout the aging process is a prominent determinant of both neuronal survival as well as survival of the entire organism.

The human brain constitutes only about 3% of one's body weight, but it requires more energy than any other organ. To generate this energy, the brain relies on mitochondrial oxidative phosphorylation, which accounts for over 90% of the cellular ATP production. Brain mitochondria consume ~20% of the total body's $O_2$ consumption at a rate of 160 µmol/100 g·min and ~15% of the human body's cardiac output. It has also been estimated that the brain utilizes ~25% of total body glucose at a rate of 31 µmol/100 g·min. The primary reason for the brain's dependence on mitochondria is of course, their high energy production efficiency. Mitochondria can generate 36 molecules of ATP for each molecule of glucose converted to $CO_2$ and $H_2O$, while glycolysis generates only 2 ATP molecules.

It is widely assumed that neuronal mitochondria are the primary consumers of $O_2$ in the brain. However, recent work has demonstrated that astrocytes account for up to 20% of the brain's $O_2$ consumption. Nuclear magnetic resonance (NMR) spectroscopy has been used to non-invasively make these measurements in the human brain, in situ. In general, metabolic fluxes are measured through neuronal and glial tricarboxylic acid (TCA) cycles. NMR studies of carbon 13 ($^{13}C$) that utilize $^{13}C$ glucose as the substrate are known to predominantly reflect neuronal metabolism. However, the relative metabolic flow between neurons and glia was still estimated at ~20% by using calculations based on animal models and cellular studies. More directly, investigators discovered that acetate was metabolized almost exclusively by glia into acetyl-CoA. Consequently, $^{13}C$ label from this substrate that accumulates in the carbon dioxide pool of mitochondria ($^{13}CO_2$) has to enter through the glial TCA cycle, since neurons do not metabolize acetate. Using this approach, investigators directly confirmed the high percentage of astroglial $O_2$ consumption in the brain. Specifically, it was estimated that the astroglial TCA cycle accounted for ~15% and 20% of the brain $O_2$ consumption, respectively.

It has been estimated that oxidative phosphorylation in cultured astrocytes contributed ~75% of the total cellular ATP synthesis. This estimate was obtained by averaging the rate of $O_2$ consumption relative to the rate of lactate production in astrocytes that was reported by several laboratories. This survey of the literature revealed that on average, cultured astrocytes consumed 14 nmol/min/mg protein of $O_2$ and synthesized 30 nmol/min/mg protein of lactate, which equates to a ratio of 74% oxidative phosphorylation to 26% glycolysis. These calculations clearly indicated that oxidative phosphorylation was a major energy source in astrocyte cultures.

Cell culture models have been used extensively to study the aging process in the central nervous system (CNS). However, the primary focus has been on the neuronal component of aging. In recent work, we addressed similar questions with regard to aging, but we focused our investigations on astrocyte physiology. Our first task was to establish and characterize primary cultures of astrocytes prepared from the brains of young (4-6 months) and old (26-28 months) mice. The cell culture procedures that we used were identical for both young and old mice. Brain issue was removed, minced and cultured in plastic T-75 flasks for the first 1-2 weeks until the cells, predominantly astrocytes, reached 70% confluency. The cultured cells were washed once with Hank's buffered saline solution to help remove non-astrocytic cells before treating the remaining plated astrocytes with a trypsin/EDTA solution for 3-5 min at 37° C. Suspended astrocytes were centrifuged, brought up in media for cell counting and plated in 35 mm dishes. The key step in this protocol was to initially plate the astrocytes at high density (10,000 cells in a 100 µl aliquot) in the center of the petric dish for ~2 hours, prior to filling the entire culture dish with media. These astrocytes were permitted to grow at least 4-7 days prior to experiments and were considered passage one cells.

Our second step in the investigation was to immunohistochemically identity the cultured cells. We used glial fibrillary acidic protein (GFAP) for astrocytes, A2B5 for type II astrocytes, GALC and RIP for immature and mature oligodendrocytes and CD11B for microglia. Essentially all of the passage one cells cultured with our protocol were GFAP positive. However, we noticed that immunoreactivity to A2B5, GALC, and RIP increased at the second passage and stabilized by the third passage, suggesting that both old and young astrocytes were becoming more undifferentiated. We also tested whether the common procedure of shaking the cultures prior to passage decreased the number of contaminating cell types like microglia. In our hands, shaking the dishes produced no significant effect on the purity of the astrocyte cultures.

The first physiological difference that we observed between astrocytes cultured from young and old astrocytes was their rate of cell growth. Astrocytes cultured from old mice exhibited significantly slower doubling rates (~30% slower). Standard hemocytometer procedures were used to make these measurements. For consistency, it was very important to maintain not only the initial cell number (100,000 cells per well of a 6 well plate), but also the same cell density. Interestingly, this difference in growth rates was still present after the cultured astrocytes had been passed up to 8 times, indicating that the underlying cause for slower growth was not significantly affected by cell passage. We speculate below that reduced mitochondrial ATP production could be partially responsible for these slower growth rates. Astrocyte cultures were eventually transformed after multiple cell passages. This transformation was easily recognized by a substantial increase in cell growth in both old and young astrocytes as well as alterations in the morphology of the cells. Astrocytes lost their characteristic star shape and assumed a more tightly packed-cobble stone appearance.

The next physiological response that we investigated during aging was intracellular $Ca^{2+}$ signaling. Metabotropic purinergic receptors (P2Y-Rs) are well known to generate robust $Ca^{2+}$ signals in astrocytes. Our initial bias was that we would observe reduced $Ca^{2+}$ responses in astrocytes cultured from old mice. Surprisingly, we found just the opposite. $Ca^{2+}$ measurements were made using standard confocal imaging of $Ca^{2+}$ sensitive fluorescent dyes, which loaded equally well for both young and old astrocytes. Bath application of ATP (1 µM) also stimulated $Ca^{2+}$ oscillations in both cultured young and old astrocytes. The first surprise finding was that a higher percentage of old astrocytes (more than half) responded to exogenously applied ATP. Two other interesting findings were that old astrocytes exhibited almost 50% higher $Ca^{2+}$ amplitudes as well as faster $Ca^{2+}$ oscillations than young astrocytes. These results appear counter intuitive, since it is reasonably expected that receptor mediated signaling is likely decreased or degraded with aging. However, we can account for these observed enhancements to cytosolic $Ca^{2+}$ signaling in old astrocytes by a reduced ability of mitochondria to sequester $Ca^{2+}$ during aging. We initially demonstrated that cytosolic $Ca^{2+}$ release was regulated by mitochondrial $Ca^{2+}$ uptake in *Xenopus* oocytes. Subsequent reports by others also demonstrated a modulatory role of mitochondria on the release of intracellular $Ca^{2+}$ in many cell-types including astrocytes, liver and HeLa cells. The ability of mitochondria to sequester $Ca^{2+}$, and thereby modulate IP3-induced $Ca^{2+}$ release, is critically dependent on the mitochondrial membrane potential ($\Delta\Psi$) and close proximity of mitochondria to the $Ca^{2+}$ release site. This proximity allows mitochondria to sense greater $Ca^{2+}$ concentrations than those present in the bulk cytosolic compartment. Consequently, a reduction in $\Delta\Psi$ with age will reduce mitochondrial $Ca^{2+}$ buffering, thereby leading to increased cytosolic $Ca^{2+}$ release and faster $Ca^{2+}$ dynamics.

As discussed above, astrocyte mitochondria are actively respiring, in vivo, and individual mitochondria can be imaged in situ using the potential sensitive dye, tetra-methyl rhodamine ethyl ester (TMRE, Molecular Probes). TMRE is positively charged and partitions itself across charged membranes in a Nerstian fashion. This permits $\Delta\Psi$ to be estimated as ~60 mV times the log of $F_{mito}/F_{cyto}$, where $F_{mito}$ is the peak fluorescent intensity observed in single mitochondrial and $F_{cyto}$ represents the lowest value of TMRE fluorescence in the cytosol. Non-specific binding of this dye is generally minimal, but can be checked by depolarizing cells with a proton ionophore (e.g. FCCP). A histogram plot of single mitochondrial values in an astrocyte revealed a range of $\Delta\Psi$s normally distributed around a mean. A similar variance in $\Delta\Psi$s was observed in both young and old astrocytes. However, older astrocytes exhibited a significantly lower mean value than young astrocytes. Furthermore, the different $\Delta\Psi$ means were maintained in astrocyte cultures for over 4 four passages of the cells. We tried to determine whether the size of a mitochondrion could be positively correlated with its $\Delta\Psi$. For these measurements, we estimated the total area of a single mitochondria as roughly equivalent to the number of continuous pixels of TMRE fluorescence. A minimal area was used in our analysis to exclude signals from random noise. We did in fact observe positive correlation. TMRE fluorescent signal (log $f_{mito}/F_{cyto}$) increased with increasing mitochondrial size and the slope of the relationship was similar for both old and young astrocytes. At higher values of mitochondrial surface area, there was no correlation. This was expected since larger areas increase the likelihood of overlapping mitochondria, which would obscure any relationship. Our only speculation regarding this relationship is that mitochondria with lower $\Delta\Psi$s may exhibit less organelle fusion. It would be interesting to test whether increased $\Delta\Psi$ results in increased fusion of smaller mitochondria as opposed to biogenesis of new mitochondrial mass. It has been demonstrated that the presence of even a few astrocytes in cultured neurons significantly increased their resistance to oxidative stress. In the next series of experiments, we wanted to determine whether the protective ability of astrocytes was affected by aging. Our initial step to test the resistance of old and young astrocytes to oxidative stress was to expose them to the oxidant stressor tert-butyl hydrogen peroxide (t-BuOOH). Cell viability was assessed by the ability of astrocytes to either retain the cytoplasmic dye, calcein AM or exclude the DNA intercalating dye, propidium iodide. Plasma membrane integrity is required to retain calcein or to exclude propidium iodide. Perhaps not surprisingly, astrocytes cultured from old animals exhibited greater sensitivity to oxidant stress when compared to young astrocytes. These experiments were followed up with an examination of the ability of astrocytes to protect neurons during aging. PC12 were differentiated with nerve growth factor for at least 7 days, until neurite processes were readily visible. Neuronal-like PC12 cells were then co-cultured with either young or old astrocytes for another 3 days before stressing them with t-BuOOH. For these experiments, we assessed cell viability by taking advantage of the potential sensitive dye TMRE. This dye only labels mitochondria that have a membrane potential, so we monitored the time required for $\Delta\Psi$ to collapse to 10% of its initial value as an indicator of cell viability. We chose 10% to insure that the TMRE fluorescence remained above its lower limit at de-energization, which is presumably due to TMRE partitioning into lipid membranes and non-specific targets. As observed in astrocyte only cultures, the time until $\Delta\Psi$ collapse was much shorter in old cells. More importantly, the time until $\Delta\Psi$ collapse in PC12 was significantly shorter when co-cultured with old astrocytes. These data represented the first direct demonstration that astrocyte neuroprotection was diminished with age. It is interesting to note that one of the characteristics of astrocytes in the aging brain is the number of astrocytes are increased by ~20%. This response has been compared to reactive gliosis in response to injured or damaged neurons during aging. However, an alternative explanation is that increased number of astrocytes in the aging brain are required to provide the same level of neuroprotection that is present in the brain of a young animal.

In the previous section, we presented a number of recent experimental findings that demonstrated diminished physiological function of astrocytes with aging. These changes are likely to contribute to or possibly cause the observed decrease in neuroprotection when co-culturing neuronal-like PC12 cells with old astrocytes. We have obtained recent data showing that the neuroprotective ability of both old and young astrocytes can be significantly increased by stimulation of purinergic G-protein coupled receptors that stimulate $IP_3$ mediated intracellular $Ca^{2+}$ release.

P2 purinoceptors are a class of cell surface receptors, subdivided into either the ligand-gated ionotropic receptors (P2X) or G-protein-coupled metabotropic receptors (P2Y)). We focused our work on the P2Y-Rs due to their strong coupling to Gq/11 signaling pathway in astrocytes. Activation of P2Y-receptors stimulates PLCB isoenzymes, increasing inositol triphosphate ($IP_3$) formation and subsequent $Ca^{2+}$ mobilization from thapsigargin sensitive stores in the endoplasmic reticulum (ER). Thapsigargin is a specific inhibitor of the sarco-endoplasmic reticulum $Ca^{2+}$ ATPases (SERCAs). As mentioned above, $IP_3$-mediated $Ca^{2+}$ release is efficiently sequestered by mitochondria, due to its physically close proximity the $Ca^{2+}$ channel pore. Increased mitochondrial $Ca^{2+}$ uptake via the $Ca^{2+}$ uniporter rapidly stimulates $Ca^{2+}$ sensitive dehydrogenases and subsequently, increases respiration and ATP production. Resting cytosolic $Ca^{2+}$ levels have in general, been shown to increase with age while the ability of mitochondria to sequester $Ca^{2+}$ appears to diminish. Our data suggest that part of the decrease in $Ca^{2+}$ uptake can be attributed to a decrease in the mitochondrial membrane potential ($\Delta\Psi$). Work has also demonstrated that the $Ca^{2+}$ uniporter itself has lower activity with age. Another important point to make with regard to mitochondrial $Ca^{2+}$ signaling is that high matrix $Ca^{2+}$ is generally thought to sensitize cells to cell death stimuli. During prolonged periods or with sufficiently high concentrations, matrix $Ca^{2+}$ induces opening of the mitochondrial permeability transition pore (MPT). Recent work has identified the mitochondrial targeted cyclophilin D as a key player in $Ca^{2+}$ stimulated cell death. We also have found that $IP_3$-induced intracellular $Ca^{2+}$ release sensitized human embryonic kidney (HEK293) cells to stimuli that induced cell death. We utilized HEK293 cells that were overexpressing type 1 muscarinic acetylcholine receptors (mAchR1s) to stimulate $IP_3$-gated $Ca^{2+}$ release. We induced apoptosis by exposing these cells to either t-BuOOH (100 μM, 3 hrs) or ceramide (40 μM, 12 hrs). Cell death was significantly higher in the presence of ACh (1 μM) for both apoptotic stimuli. Thus, it was quite clear that stimulation of $IP_3$-gated $Ca^{2+}$ release can have activate both cell survival (ATP production) and cell death (MTP opening) pathways in cells. As will be presented in the following section, the $IP_3$-activated cell survival pathway is dominate in astrocytes.

To determine whether activation of P2Y-Rs would stimulate cell death or enhance cell survival, we exposed astrocytes to a bolus of extracellular ATP. Cultures were then washed with normal saline and perfused with the oxidant stressor t-BuOOH. Cell viability was assessed by monitoring the $\Delta\Psi$ with the potential sensitive dye TMRE. Surprisingly, a brief 10-minute of ATP, prior to oxidant stress treatment, delayed the time until $\Delta\Psi$ collapse for several hours in both old and young astrocytes. These data demonstrated that activation of purinergic receptors enhanced a cell survival signaling pathway and not cell death. Another interesting point regarding ATP enhanced resistance to oxidant stress was that the time until $\Delta\Psi$ collapse for old astrocytes was increased nearly to the level of young astrocytes. This suggested that the same protective mechanism was not only present in older cells, but that it could be activated to such an extent as to be comparable to stimulated young astrocytes. We immediately began investigating the role of intracellular $Ca^{2+}$ in this protective mechanism because of the known coupling of purinergic receptors to these signaling pathways.

Experiments were again carried out in cultures of astrocytes from young and old mice. We utilized the $Ca^{2+}$ indicator dye Fura 2 AM to measure $Ca^{2+}$, since this indicator works well with 2-photon excitation at 800 nm (the peak power of Ti-Sapphire lasers) and could be used to simultaneously monitor $\Delta\Psi$ with TMRE. A disadvantage of using 2-photon excitation for Fura-2 is that absorption at this wavelength is strong only for the $Ca^{2+}$ free form of Fura-2. Consequently, Fura-2 ratioing is not possible and Ca2+ increases are recorded as decreases in cellular fluorescence, normalized to the resting fluorescence. Using this experimental procedure, we confirmed that application of extracellular ATP stimulated a large increase in intracellular $Ca^{2+}$, as expected from the numerous reports of other investigators as well as our earlier work. We next utilized a competitive antagonist of the $IP_3R$, xestospongin C (XeC), to begin testing whether the metabotropic P2Y-R signaling cascade was involved in ATP-enhanced resistance to oxidative stress. Consistent with the involvement of this pathway, astrocytes pretreated with XeC exhibited a significant decrease in ATP-induced $Ca^{2+}$ responses Inhibition was not complete since a large proportion of purinergic $Ca^{2+}$ increases in astrocytes is also due to influx through plasma membrane P2X receptor ion channels. Nevertheless, ATP-enhanced resistance to oxidative stress of astrocytes treated with XeC was completely blocked. We interpreted this data as strong evidence that the metabotropic P2Y receptor pathway, via stimulation of $IP_3Rs$, was required to enhance astrocyte resistance against oxidant stress.

To directly examine the role of $IP_3$ gated $Ca^{2+}$ release in P2Y-R enhanced astrocyte protection, we used a membrane permeant butyryloxymethyl ester of $IP_3$ ($IP_3$-BM). Cultures of astrocytes were exposed to $IP_3$-BM and $Ca^{2+}$ levels were assessed using 2-photon imaging of Fura 2. $Ca^{2+}$ increases in response to $IP_3$-BM application were easily detected, but they occurred over a much slower time course than those initiated by ATP treatment. This was not unexpected because of the slow process of $IP_3$-BM movement across the lipid bilayer as well as the time needed to cleave the ester and accumulate $IP_3$ in the cell. Because of the slower time course, we pretreated astrocytes for 20 minutes prior to exposing them to the oxidant stress t-BuOOH. Again, we found $IP_3$-BM pretreatment to be protective, significantly delaying the time until $\Delta\Psi$ collapsed. Similarly, $IP_3$-BM treatment enhanced the resistance of old astrocytes to levels nearly equivalent to treated young astrocytes. The protective effect of $IP_3$-BM treatment was blocked by the $IP_3R$ inhibitor, XeC. Aside from confirming that P2Y-R enhanced resistance of astrocytes was due to metabotropic signaling, these results further suggested that increased protection could be activated by any G-protein coupled receptor that stimulated $IP_3$-gated intracellular $Ca^{2+}$ release. In this light, we note that it is well established that glutamate stimulates $Ca^{2+}$ release and $Ca^{2+}$ waves across cultured astrocytes. The type 5 metabotropic glutamate receptor (mGlu5R) appears to be the predominant isoform in astrocytes that stimulates $IP_3$-gated $Ca^{2+}$ release and it is abundantly expressed throughout the cortex. To test if metabotropic glutamate receptor (mGluR) activation was also capable of enhancing astrocyte resistance to oxidative stress, we pretreated astrocytes with the general mGluR-$IP_3$ generating agonist 1S,3R-ACPD for 10 minutes. Data generated from these preliminary experiments are unpublished. However, ACPD treatment increased the % of astrocytes alive after 4 hours of t-BuOOH treatment to 66+9% (mean+SD, n=89 total cells, pooled from 8 imaging fields) compared to control, untreated astrocytes, which exhibited 38+8% (n=85 total cells, pooled from 6 imaging fields) of its cell alive. ACPD enhancement was virtually indistinguishable from P2Y-R enhanced resistance at 65+8 (n=79 total cells, pooled from 6 imaging fields). Taken together, these data strongly indicated that any receptor-mediated process that preferentially stimulated $IP_3$ mediated $Ca^{2+}$ release in astrocytes could enhance their resistance to oxidative stress.

Mitochondrial oxidative phosphorylation is widely recognized as the primary mechanism of energy production in neurons and which requires both oxygen and glucose to produce ATP. As discussed above, the fact that astrocytes also rely predominantly on oxidative metabolism is not as widely appreciated. Astrocytes contribute significantly $O_2$ consumption in the brain and decreases in $O_2$ are certain to inhibit and/or completely block oxidative phosphorylation. The link between intracellular $Ca^{2+}$ signaling and mitochondrial energy production has also been well established. Increasing matrix $Ca^{2+}$ stimulates $Ca^{2+}$ sensitive dehydrogenases in the citric acid cycle. This, in turn, increases the supply of reducing equivalents to the respiratory chain and ultimately, increases ATP production. To test whether P2Y-R enhanced resistance to oxidative stress was dependent on mitochondria, we utilized oligomycin, a specific inhibitor of the mitochondrial ATP synthetase. Pretreating astrocytes with oligomycin prior to oxidant stress did not alter $\Delta\Psi$ in young or old astrocytes compared to untreated control astrocytes. This suggested that resting energy metabolism in astrocytes was largely independent of oxidative metabolism. However, oligomycin treatment of astrocytes completely blocked P2Y-R enhanced protection of astrocytes in both old and young astrocytes. We interpreted these data as strong evidence for a role of astrocyte mitochondria metabolism in P2Y-R enhanced protection. To further test this hypothesis, we measured both $O_2$ consumption and ATP production in astrocytes with or without P2YR stimulation.

Cultured astrocytes were gently suspended in buffer and placed in a Respirometer Chamber maintained at 37° C. As compared to buffer alone, we saw a steady decline in the $O_2$ content of the chamber, indicating resting mitochondrial oxidative phosphorylation. More importantly, when we added ATP to the chamber, we saw a significant increase in the rate of $O_2$ consumption. Oligomycin treatment blocked the ATP mediated increase in $O_2$ consumption, further supporting the hypothesis that P2Y-R stimulation was increasing mitochondrial metabolism. Next, we directly measured intracellular ATP levels in astrocytes using a standard luciferine-luciferase assay. Cultured cells were rapidly heated to 100° C. to minimized enzymatic changes in intracellular ATP levels. To avoid contaminating problems with extracellular ATP in our measurements, we treated astrocytes with a P2Y1-R specific ligand, 2-MeSADP. As will be discussed below, this ligand also increased the resistance of astrocytes to oxidative stress. We found that P2Y1-R activation significantly increased intracellular ATP levels. Interestingly, when we pretreated cultured cells with oligomycin, we noticed a significant reduction in resting ATP levels, suggesting that mitochondria contributed a large portion of astrocyte energy even under resting conditions. Furthermore, P2Y1-R activation via 2-MeSADP did not increase ATP levels in the presence of oligomycin. We generated additional supporting evidence for $IP_3$-activated $Ca^{2+}$ stimulated mitochondrial ATP production when we pre-treated astrocytes with ruthenium 360 ($Ru_{360}$), an inhibitor of the electrogenic mitochondrial $Ca^{2+}$ uniporter. $Ru_{360}$ treatment also lowered resting levels of ATP and completely blocked P2Y-R stimulated ATP increases. As a final test for the involvement of mitochondria, we measured $\Delta\Psi$ with TMRE using 2-photon imaging. In single astrocytes, the same field of mitochondria was imaged before and 10 minutes after ligand treatment. We found that astrocyte $\Delta\Psi$ were significantly increased when astrocytes were treated with extracellular ATP or membrane permeant $IP_3$-BM. No changes were observed when astrocytes were exposed to a bolus of buffer alone or in astrocytes that had been pretreated with XeC. Taken together, these data strongly indicated the P2Y-R activation stimulated mitochondrial ATP production in cultured astrocytes. Given the ability of $IP_3$-BM alone to increase $\Delta\Psi$ or enhance astrocyte resistance to oxidative stress, we also anticipate that other G-protein coupled receptors will similarly increase mitochondrial energy production in astrocytes.

Our initial experiments investigating the efficacy of astrocytes to increase the resistance of neuronal-like PC12 cells to oxidative stress clearly suggested that old astrocytes were not as neuroprotective as young astrocytes. We next took advantage of a co-culture system that physically separated astrocytes from neurons. Primary cortical neurons were cultured on the glass bottoms of 6-well mat-tek plates, while primary astrocyte cultures were plated in the transwell-clear permeable supports. In this configuration, astrocytes are separated from the neurons by ~1 mm A significant advantage of this configuration is that we could separate out the contribution of P2Y-R activation in co-cultures as well as neuron only cultures, since the transwell supports containing astrocytes could be physically removed just prior to ligand treatments. Astrocyte cultures were initially established in the transwell supports for 7-10 days or until ~70% confluency. Cortical neurons were then plated in the glasswell bottoms, allowed to settle for ~1-2 hour and then a transwell support with cultured astrocytes was placed in each well. The co-cultures were maintained together for four days prior to experiments in a neurobasal medium supplemented with L-glutamine, penicillin/streptomycin, and B-27. The B-27 was added to control glia contamination. The effect of this supplement on astrocyte neuroprotection is discussed below. To measure the efficacy of astrocyte neuroprotection, we again induced oxidant stress in the cell cultures with t-BuOOH treatment. Cell viability was measured after 4 hours of t-BuOOH treatment by determining the co-localization of cells stained with Hoechst 33342 and calcein AM. Our immediate goal was to check whether pre-treatment with purinergic ligands ATP, 2 MeSADP (P2Y1-R specific ligand) or UTP (P2Y2-R specific ligand) enhanced neuronal viability during oxidative stress. We found that all three purinergic ligands exhibited a comparable ability to enhance the resistance of cortical neurons against oxidant stress. These data confirmed that purinergic activation was protective for culture embryonic cortical neurons. They also again implied that at least in cell culture, any receptor isoform that preferentially stimulates $IP_3$-mediated $Ca^{2+}$ release in astrocytes has the potential to be neuroprotective. Interestingly, it is known that the specific $Ca^{2+}$ responses of each P2Y-R isoform have two distinct types of activity-dependent negative feedback. $Ca^{2+}$ responses that are mediated by $P2Y_1$-R5 appear more oscillatory, which has been shown in other systems to be more effective at stimulating mitochondrial metabolism. Consequently, we were interested to know whether one isoform was more protective than the other. However, our current data did not support a differential protective effect based on the pattern or dynamics of $Ca^{2+}$ releases, although a more thorough investigation applying a range of ligand concentrations will be needed to carefully address this issue. Along the lines of receptor specificity, it is also interesting to note that ATP-stimulated $Ca^{2+}$ waves in astrocytes result in the release of glutamate from astrocytes. As noted above, the mGluR agonist ACPD increased astrocyte resistance to oxidative stress and consequently, this ligand has the potential of being neuroprotective.

Use of the transwell configured co-culture system permitted us to make several additional observations. First, data collected from these experiments revealed that neuroprotection was being mediated by a soluble factor, since the astrocytes were separated from the neurons by ~1 mm Second, the transwell configuration allowed us to separate out the effects of purinergic signaling on astrocytes versus neurons. Purinergic receptor (P2X) activation in the brain has been reported to enhance neuronal cell death. To investigate this, we compared the effect of purinergic ligand stimulation in co-cultures versus neuron only cultures that had been treated with ligand and t-BuOOH after removal of the astrocyte transwell. Purinergic receptor activation with ATP in neuron only cultures was not protective and actually increased cell death. On the other hand, pre-treatment of neuron only cultures with the P2Y1-R specific ligand, 2MeSADP, had no effect on neuronal viability. These data were consistent with previous reports that the toxic effect of ATP treatment on neurons was due to the activation of P2X-Rs. Interestingly, these data also revealed that while pre-treatment of co-cultures with ATP activates purinergic receptors on both astrocytes and neurons, the dominant effect of extracellular ATP during oxidative stress was protection mediated by P2Y-R activation on astrocytes.

When we initially examined the protective efficacy of old versus young astrocyte in co-cultures with cortical neurons, we were surprised by the observation that old astrocytes were just as neuroprotective as young astrocytes. Multiple experiments confirmed that these data were accurate. We finally accounted for this apparent discrepancy when we carefully considered the co-culture media being used to support astrocyte-neuronal co-cultures. Unlike, astrocyte co-cultures with PC12 cells, co-cultures with isolated cortical neurons required that we include in the culture medium a supplement to suppress glial contamination. In short, the B-27 supplement that was used for this purpose contained antioxidants, which presumably were incorporated into the cortical neurons and made astrocytes much more resistant to oxidative stress. Fortunately, the commercial company we obtained this supplement from offered a B-27 formulation that was antioxidant free. Utilizing this supplement in our co-culture experiments, we repeated the neuroprotection assays and confirmed that old astrocytes co-cultured with cortical neurons were much more sensitive to oxidative stress. A 3 hour incubation period with t-BuOOH resulted in ~70% neuronal death compared to the ~30% neuronal death for 4 hours of treatment with t-BuOOH using B-27 supplement with antioxidants. P2Y-R activation still enhanced neuroprotection, which could be completely blocked by oligomycin treatment. In addition, neurons that were pre-cultured with astrocytes and exposed to ATP also exhibited more cell death. These data confirmed the contaminating effect of anti-oxidants in estimating the neuroprotective efficacy of astrocytes.

The work that we have discussed up to this point demonstrate that the maintenance and stimulation of mitochondrial metabolism enhances astrocyte resistance to oxidative stress and increases their ability to protect neurons throughout the aging process. We note that the primary energy-consuming process in the brain is the maintenance of ion concentration gradients across the plasma membrane. These gradients are generally maintained by energy-dependent pumps. Of these, it has been estimated that the $Na^+/K^+$ ATPase by itself consumes ~20% of the astrocytic ATP levels in order to maintain $Na^+$ and $K^+$ homeostasis. Astrocyte ATP levels are also diminished during excitatory glutaminergic synaptic transmission. Glutamate recycling begins with $Na^+$ dependent uptake at a cost of 3 $Na^+$ ions per glutamate molecule transported. The increased intracellular $Na^+$ stimulates $Na^+/K^+$ ATPase activity to restore the ion gradients at a stochiometry of 3 $Na^+$ ions pumped out for every to 2 $K^+$ ions pumped into the cell. Glutamate is then converted to glutamine by the glutamine synthase. Two ATP molecules are consumed during this process; one by the ATPase and another is used by the synthase. It is generally assumed that these ATP molecules are produced from a single glucose molecule going through glycolysis, which attractively generates two ATP molecules. While this energy source is certainly possible, the reported data do not exclude energy contributions from oxidative phosphorylation. Evidence clearly shows that the glutamate/glutamine neurotransmitter cycle is dependent on increased $Na^+/K^+$ ATPase activity, since cycling can be completely inhibited by ouabain, a specific inhibitor of this pump. It is also clear from reported studies that glucose utilization is stimulated during the process of glutamate recycling in the astrocyte. In some studies, energy production was highly compartmentalized because of a comparatively simple nervous tissue in their preparation, the honeybee retina. In this organ, the photoreceptors (neurons) contain large numbers of mitochondria whereas the glial cells are nearly devoid of these organelles. Consequently, energy metabolism in honeybee glial cells is almost exclusively glycolytic, which transfers carbohydrates as energy substrates to the neurons for aerobic metabolism. The main point for this discussion is that the separation of metabolic functions is not nearly as compartmentalized in the mammalian brain. As discussed earlier, astrocyte mitochondria are prevalent, active and during intense periods of neuronal activity, it would be expected that oxidative phosphorylation would be an important source of ATP for glutamate recycling.

Another important load on astrocyte energy metabolism is the synthesis of glutathione (GSH). The thiol moiety of GSH is used as a substrate for glutathione peroxidase (Gpx) enzymes, which is the predominant mechanism to reduce $H_2O_2$ and lipid hydroperoxides. GSH is a key antioxidant in the resistance of both astrocytes and neurons during oxidative stress. Importantly, neuronal GSH production is critically dependent on GSH production in astrocytes, which contain significantly higher concentrations of GSH than neurons. Maintenance of astrocyte GSH levels is controlled by two ATP-dependent enzymes. Glutamate cysteine ligase (GCL) is the rate limiting enzyme composed of a catalytic subunit (GCLc) and a modulatory subunit (CCLm). GCL activity increases during oxidative stress and produces γ-glutamyl cysteine (γ-glu-cys). Glutathione synthetase (GS) is the second major enzyme that combines γ-glu-cys with glycine (gly) to produce GSH. GSH efflux from astrocytes appears to be controlled, in large part, by the multidrug resistance protein type 1 (MRP1). Once exported, GSH is cleaved by the ectoenzyme γ-glutamyl transpeptidase (γGT) producing a glutamyl moiety and the dipeptide cysteinylglycine (cys-gly). Cysteinylglycine is then cleaved by aminopeptidase N (ApN) to produce cysteine. Neuronal de novo synthesis of GSH is dependent on this rate limiting source of cysteine. During oxidative stress, GSH levels in both astrocytes and neurons would be rapidly depleted and ATP dependent de novo GSH synthesis would be needed. If ATP production became rate limiting, one possible mechanism by which P2Y-R enhanced astrocyte neuroprotection could be mediated is by stimulation of oxidative phosphorylation. As noted above, $Ca^{2+}$ stimulated mitochondrial ATP production in cardiac cells is very rapid, occurring ~10× faster than stimulation by increased ADP levels. In contrast, glycolysis may not be able to generate sufficient quantities of ATP during acute periods of stress.

Irrespective of the precise underlying cause of aging, it is clear that mitochondria play key roles in regulating cell survival via energy production in the brain. This well characterized physiological function has long been accepted for neuronal cells. The precise roles of astrocyte mitochondrial metabolism on the other hand, have generally not been as fully appreciated. We have discussed evidence that astrocyte mitochondrial metabolism does in fact, play a pivotal role in the brain throughout the aging process. Not surprisingly, we discovered that the aging process itself degrades astrocyte mitochondria function, astrocyte resistance to oxidative stress as well as the neuroprotective abilities of astrocytes. Remarkably, the ability of astrocytes to enhance their protective functions could be significantly enhanced even in old cells. The underlying mechanism of enhanced protection was mediated by $Ca^{2+}$ stimulated mitochondrial metabolism. The source of this $Ca^{2+}$ was $IP_3$-activated intracellular $Ca^{2+}$ release from the endoplasmic reticulum. While this pathway was primarily controlled by puringeric receptors in our studies, it is clear that any other receptor that preferentially stimulates $IP_3$ production in astrocytes is likely to be an effective enhancer of neuroprotection. The potential therapeutic benefits of activating this pathway are numerous. We noted that aged astrocytes were more sensitive to oxidative stress and exhibited decreased neuroprotection under non-stimulated conditions. Activation of the P2Y-R signaling pathway enhanced protection to levels that were comparable to stimulated young astrocytes. Consequently, any G-protein coupled receptors that stimulate mitochondrial ATP production could be used to minimize stress during aging as well as enhance astrocyte protective functions in various neurodegenerative disorders that have been correlated with increased oxidative damage including Alzheimer's Disease (AD), Parkinson's Disease (PD) and amyotrophic lateral sclerosis (ALS).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the claims appended hereto.

What is claimed is:

1. A method of treating cerebral trauma in a subject comprising: administering to a subject in need of such treatment a pharmaceutical composition comprising a therapeutically effective amount of a nucleotide diphosphate having the structure,

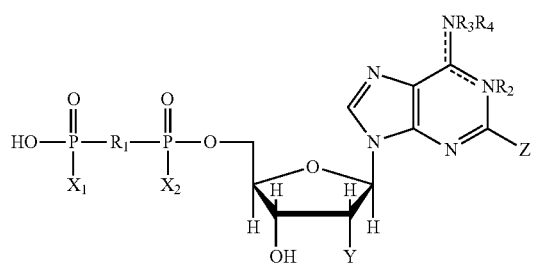

wherein: $X_1$, and $X_2$ are each independently either —OH, —O⁻, —SH, or —S⁻;

Y is H or OH;

$R_1$ is O, imido, methylene, or dihalomethylene;

Z is Cl or SR, wherein R is $C_1$-$C_{20}$ saturated alkyl or $C_1$-$C_{20}$ unsaturated alkyl;

$R_3$ and $R_4$ are H while $R_2$ is nothing and there is a double bond between N-1 and C-6 (adenine), or $R_3$ and $R_4$ are H while $R_2$ is nothing and Z is SR, or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,N6-ethenoadenine);

wherein the pharmaceutical composition is effective to increase the extracellular concentration of the nucleotide diphosphate in the central nervous system of the subject such that at least a portion of astrocytes in the affected area of the CNS initiate $IP_3$-mediated $Ca^{2+}$ release and mount a neuroprotective response.

2. The method of claim 1, wherein the nucleotide diphosphate is 2-methylthio adenosine 5'-diphosphate (2-MeSADP) or N-methanocarba-2-methylthio adenosine 5'-diphosphate ("MRS2365").

3. The method in accordance with claim 1, wherein the pharmaceutical composition is administered to the subject within 24 hours of cerebral trauma.

4. The method in accordance with claim 1, wherein the pharmaceutical composition is administered to the subject within 6 hours of cerebral trauma.

5. The method in accordance with claim 1, wherein the pharmaceutical composition is administered to the subject within 1 hour of cerebral trauma.

6. The method in accordance with claim 1, wherein the pharmaceutical composition is administered to the subject within 30 minutes of cerebral trauma.

7. The method in accordance with claim 1, wherein the pharmaceutical composition is administered to the subject within 10 minutes of cerebral trauma.

8. The method in accordance with claim 1, wherein the pharmaceutical composition is administered to the subject orally.

9. The method in accordance with claim 1, wherein the pharmaceutical composition is administered to the subject parenterally.

10. A method of treating cerebral trauma in a subject comprising: administering to a subject in need of such treatment a pharmaceutical composition comprising a therapeutically effective amount of a compound having the structure:

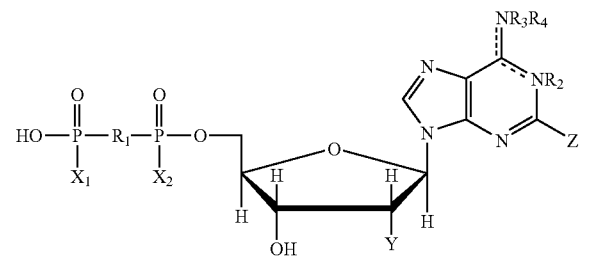

wherein: $X_1$, and $X_2$ are each independently either —OH;
Y is OH;
$R_1$ is O;
Z is Cl or SR, wherein R is $C_1$-$C_{20}$ saturated alkyl or $C_1$-$C_{20}$ unsaturated alkyl;
$R_3$ and $R_4$ are H while $R_2$ is nothing and there is a double bond between N-1 and C-6 (adenine), or
$R_3$ and $R_4$ are H while $R_2$ is nothing and Z is SR, or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,N6-ethenoadenine).

11. A method of treating cerebral trauma in a subject comprising: administering to a subject in need of such treatment a pharmaceutical composition comprising a therapeutically effective amount of a nucleotide diphosphate or a nucleotide triphosphate, wherein said amount is effective to increase the extracellular concentration of said agent in the central nervous system of the subject such that at least a portion of the astrocytes in the affected area of the CNS initiate $IP_3$-mediated $Ca^{2+}$ release and mount a neuroprotective response.

12. The method of claim 11, wherein the pharmaceutical composition comprises a nucleotide diphosphate having the structure:

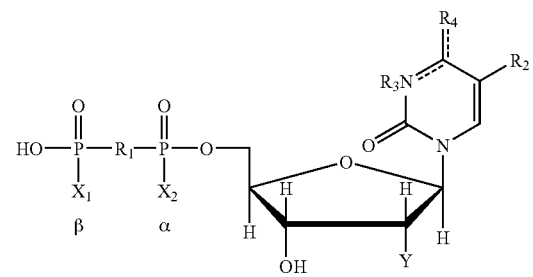

wherein: $X_1$, and $X_2$ are each independently either —OH, —O⁻, —SH, or —S⁻;

Y is H or OH;

$R_1$ is O, imido, methylene, or dihalomethylene;

$R_2$ is H, halogen, alkyl, substituted alkyl, alkoxyl, nitro or azido;

$R_3$ is nothing, H, alkyl, acyl, arylacyl, or arylalkyl; and $R_4$ is —OR', —SR', NR', and NR'R", wherein R' and R" are independently H, alkyl, substituted alkyl, aryl, substituted aryl, arylalkyl, alkoxyl, or aryloxyl, and R' is absent when $R^4$ is double bonded from an oxygen or sulfur atom to the carbon at the 4-position of the pyrimidine ring.

13. The method of claim 12, wherein the nucleotide diphosphate is uridine 5'-diphosphate (UDP); uridine 5'—O—(2-thiodiphosphate)(UDPBS); 5-bromouridine 5'-diphosphate (5-BrUDP); 5- (1-phenylethynyl)-uridine 5'-diphosphate (5- (1-phenylethynyl)UDP) ; 5-methyluridine 5'-diphosphate (5-methylUDP); 4-hexylthiouridine 5'-diphosphate (4- hexylthioUDP); 4-mercaptouridine 5'-diphosphate (4-mercaptoUDP); 4-methoxyuridine 5'-diphosphate (4-methoxyUDP); 4-(N-morpholino)uridine 5'-diphosphate (4-(N-morpholino)UDP;

4-hexyloxyuridine 5'-diphosphate (4-hexyloxyUDP); N,N-dimethylcytidine 5'-diphosphate (N,N-dimethylCDP); N-hexylcytidine 5'-diphosphate (N-hexylCDP); or N-cyclopentylcytidine 5'-diphosphate (N-cyclopentylCDP).

14. The method of claim 11, wherein the pharmaceutical composition comprises a nucleotide triphosphate having the structure:

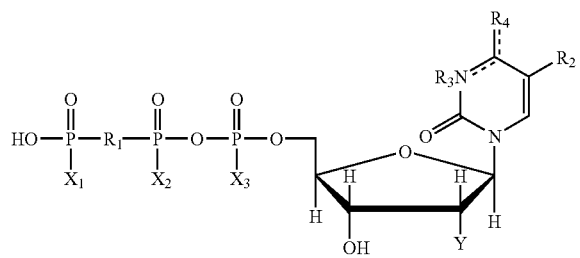

wherein: $X_1$, $X_2$ and $X_3$ are each independently either —OH, —O⁻, —SH, or —S⁻;
Y is H or OH;
$R_1$ is O, imido, methylene, or dihalomethylene;
$R_2$ is H, halogen, alkyl, substituted alkyl, alkoxyl, nitro or azido;
$R_3$ is nothing, H, alkyl, acyl, arylacyl, or arylalkyl; and
$R_4$ is —OR', —SR', NR', and NR'R", wherein R' and R" are independently H, alkyl, substituted alkyl, aryl, substituted aryl, arylalkyl, alkoxyl, or aryloxyl, and R' is absent when $R^4$ is double bonded from an oxygen or sulfur atom to the carbon at the 4-position of the pyrimidine ring.

15. The method of claim 14, wherein the nucleotide triphosphate is uridine 5'-triphosphate (UTP) or uridine 5'—O—(3-thiotriphosphate) (UTPγS).

16. The method of claim 11, wherein the pharmaceutical composition comprises a nucleotide diphosphate having the structure:

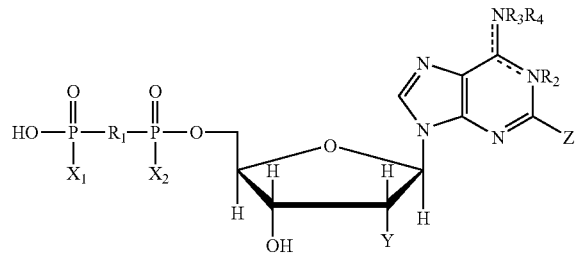

wherein: $X_1$, and $X_2$ are each independently either —OH, —O⁻, —SH, or —S⁻;
Y is H or OH;
$R_i$ is O, imido, methylene, or dihalomethylene;
Z is H, Cl, or SR, wherein R is alkyl ($C_1$-$C_{20}$, saturated or unsaturated);
$R_3$ and $R_4$ are H while $R_2$ is nothing and there is a double bond between N-1 and C-6 (adenine), or
$R_3$ and $R_4$ are H while $R_2$ is nothing and Z is SR, or
$R_3$ and $R_4$ are H while $R_2$ is O and there is a double bond between N-1 and C-6 (adenine 1-oxide), or
$R_3$, $R_4$, and $R_2$ taken together are —CH═CH—, forming a ring from N-6 to N-1 with a double bond between N-6 and C-6 (1,N6-ethenoadenine).

17. The method of claim 16, wherein the nucleotide diphosphate is 5'-adenosine diphosphate (ADP), 2-methylthio adenosine 5'-diphosphate (2-MeSADP) or N-methanocarba-2-methylthio adenosine 5'-diphosphate ("MRS2365").

18. The method of claim 11, wherein the pharmaceutical composition comprises a nucleotide triphosphate having the structure:

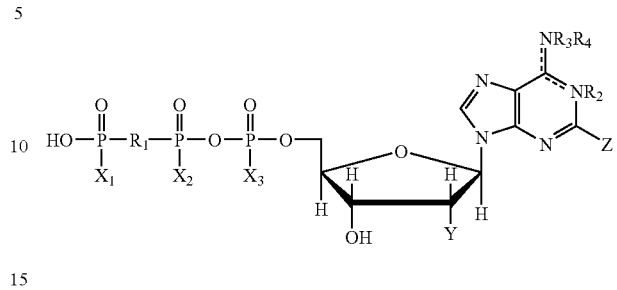

wherein: $X_1$, $X_2$ and $X_3$ are each independently either —OH, —O⁻, —SH, or —S⁻;
Y is H or OH;
$R_1$ is O, imido, methylene, or dihalomethylene;
Z is H, Cl, or SR, wherein R is alkyl ($C_1$-$C_{20}$, saturated or unsaturated);
$R_3$ and $R_4$ are H while $R_2$ is nothing and there is a double bond between N-1 and C-6 (adenine), or
$R_3$ and $R_4$ are H while $R_2$ is nothing and Z is SR, or
$R_3$ and $R_4$ are H while $R_2$ is O and there is a double bond between N-1 and C-6 (adenine 1-oxide), or
$R_3$, $R_4$, and $R_2$ taken together are —CH═CH—, forming a ring from N-6 to N-1 with a double bond between N-6 and C-6 (1,N6-ethenoadenine).

19. The method of claim 11, wherein the pharmaceutical composition comprises a nucleotide diphosphate having the structure:

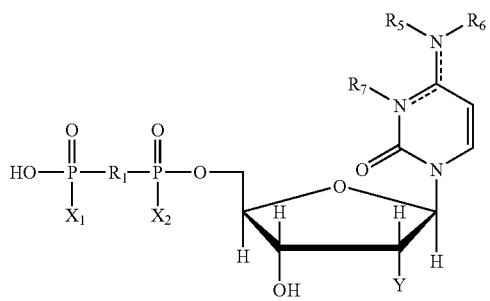

wherein: $X_1$, and $X_2$ are each independently either —OH, —O⁻, —SH, or —S⁻;
Y is H or OH;
$R_1$ is O, imido, methylene, or dihalomethylene;
$R_5$ and $R_6$ are H while $R_7$ is nothing and there is a double bond between N-3 and C-4 (cytosine), or
$R_5$ and $R_7$ taken together are —CH═CH—, forming a ring from N-3 to N-4 with a double bond between N-4 and C-4 (3,N4-ethenocytosine), optionally the hydrogen of the 4- or 5-position of the etheno ring is substituted with alkyl, substituted alkyl, aryl; substituted aryl (heteroaryl, etc.), alkoxyl, nitro, halogen, or azido.

20. The method of claim 11, wherein the pharmaceutical composition comprises a nucleotide triphosphate having the structure:

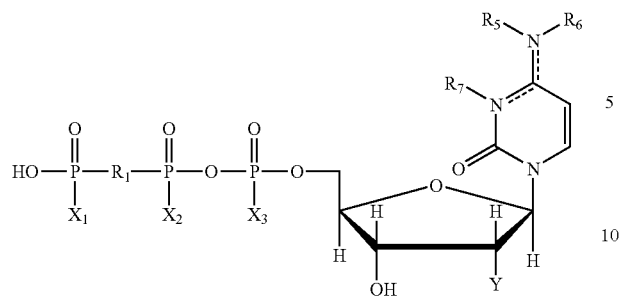

wherein: $X_1$, $X_2$ and $X_3$ are each independently either —OH, —O$^-$, —SH, or —S$^-$;

Y is H or OH;

$R_1$ is O, imido, methylene, or dihalomethylene;

$R_5$ and $R_6$ are H while $R_7$ is nothing and there is a double bond between N-3 and C-4 (cytosine), or $R_5$ and $R_7$ taken together are —CH=CH—, forming a ring from N-3 to N-4 with a double bond between N-4 and C-4 (3,N4-ethenocytosine), optionally the hydrogen of the 4- or 5-position of the etheno ring is substituted with alkyl, substituted alkyl, aryl; substituted aryl (heteroaryl, etc.), alkoxyl, nitro, halogen, or azido.

21. The method of claim 20, wherein the nucleotide triphosphate is cytidine 5'-triphosphate (CTP) and 4-nitrophenyl ethenocytidine 5'-triphosphate.

* * * * *

UNITED STATES PATENT AND TRADEMARK OFFICE
CERTIFICATE OF CORRECTION

| | |
|---|---|
| PATENT NO. | : 8,618,074 B2 |
| APPLICATION NO. | : 12/531410 |
| DATED | : December 31, 2013 |
| INVENTOR(S) | : James D. Lechleiter |

It is certified that error appears in the above-identified patent and that said Letters Patent is hereby corrected as shown below:

In the Specification:

Please add the following paragraph before the priority claim information beginning at line 4 of Col. 1:

REFERENCE TO GOVERNMENT SPONSORED RESEARCH

The invention set forth herein was funded at least in part by funds granted by the National Institutes of Health Grant No. PO1 AG19316. The United States government may therefore be entitled to certain rights in this invention.

Signed and Sealed this
Third Day of February, 2015

Michelle K. Lee
*Deputy Director of the United States Patent and Trademark Office*